(12) United States Patent
Page et al.

(10) Patent No.: US 10,940,304 B2
(45) Date of Patent: *Mar. 9, 2021

(54) MIXING SYSTEMS AND METHODS FOR RESEARCH, INDUSTRIAL AND MEDICAL USES

(71) Applicant: Intravenous Solutions, Ltd., Sayville, NY (US)

(72) Inventors: Christopher Page, Rye Brook, NY (US); Stephen Probst, Stony Brook, NY (US); Thomas Corrado, Ronkonkoma, NY (US)

(73) Assignee: Intravenous Solutions, Ltd., Sayville, NY (US)

( * ) Notice: Subject to any disclaimer, the term of this patent is extended or adjusted under 35 U.S.C. 154(b) by 185 days.

This patent is subject to a terminal disclaimer.

(21) Appl. No.: 16/048,593

(22) Filed: Jul. 30, 2018

(65) Prior Publication Data

US 2018/0333567 A1    Nov. 22, 2018

Related U.S. Application Data

(60) Division of application No. 14/623,029, filed on Feb. 16, 2015, now abandoned, which is a continuation of
(Continued)

(51) Int. Cl.
*A61M 39/08* (2006.01)
*B01F 5/04* (2006.01)
(Continued)

(52) U.S. Cl.
CPC .......... *A61M 39/08* (2013.01); *A61M 5/1407* (2013.01); *A61M 39/286* (2013.01);
(Continued)

(58) Field of Classification Search
CPC .. A61M 3/005; A61M 5/1407; A61M 5/1408; A61M 39/08; A61M 2039/0027;
(Continued)

(56) References Cited

U.S. PATENT DOCUMENTS

| 822,379 A | 6/1906 | Luckenbach |
|---|---|---|
| 1,453,385 A | 5/1923 | Dzutsoff |

(Continued)

OTHER PUBLICATIONS

International Search Report and Written Opinion from International Patent Application No. PCT/US2011/062671.
(Continued)

*Primary Examiner* — Kami A Bosworth
(74) *Attorney, Agent, or Firm* — Eric L. Lane; Green Patent Law

(57) ABSTRACT

Mixing systems and methods include a mixing device comprising a primary tube having a proximal end, a distal end, an outer surface and an inner lumen and at least one secondary tube having a proximal end, a distal end, an outer surface and an inner lumen. The at least one secondary tube is substantially parallel to the primary tube. The distal end of the at least one secondary tube is fluidly connected to the primary tube at a junction located on the primary tube close to the distal end of the primary tube.

19 Claims, 31 Drawing Sheets

Related U.S. Application Data application No. 12/960,375, filed on Dec. 3, 2010, now Pat. No. 8,968,238.

(51) Int. Cl.
  *A61M 5/14* (2006.01)
  *A61M 39/28* (2006.01)
  *A61M 39/24* (2006.01)

(52) U.S. Cl.
  CPC ............ B01F 5/0403 (2013.01); B01F 5/048 (2013.01); *A61M 2039/082* (2013.01); *A61M 2039/2406* (2013.01); *Y10T 137/0318* (2015.04); *Y10T 137/87571* (2015.04); *Y10T 137/87676* (2015.04)

(58) Field of Classification Search
  CPC ............ A61M 2039/082; B01F 5/0403; B01F 5/0405; B01F 5/0471; Y10T 137/87571; Y10T 137/87652
  See application file for complete search history.

(56) References Cited

U.S. PATENT DOCUMENTS

| | | | |
|---|---|---|---|
| 1,504,851 A | | 8/1924 | Wren |
| 2,893,646 A | * | 7/1959 | Batts .................... B05B 7/04 239/419.3 |
| 3,729,032 A | * | 4/1973 | Tischlinger ......... A61M 5/1782 141/2 |
| 3,750,875 A | | 8/1973 | Juster |
| 4,191,183 A | | 3/1980 | Mendelson |
| 4,405,313 A | | 9/1983 | Sisley |
| 4,634,092 A | * | 1/1987 | Daniell ................ A61M 39/28 251/7 |
| 4,846,405 A | | 7/1989 | Zimmermann |
| 4,968,307 A | | 11/1990 | Dake et al. |
| 5,041,087 A | | 8/1991 | Loo et al. |
| 5,211,627 A | | 5/1993 | Howat |
| 5,364,377 A | | 11/1994 | O'Neil |
| 5,833,652 A | | 11/1998 | Preissman et al. |
| 5,891,100 A | | 4/1999 | Fleckenstein |
| 5,984,889 A | | 11/1999 | Christ et al. |
| 6,234,993 B1 | | 5/2001 | Terpilowski et al. |
| 2002/0099326 A1 | * | 7/2002 | Wilson .............. A61M 25/0097 604/43 |
| 2003/0130617 A1 | | 7/2003 | Leone |
| 2006/0064051 A1 | | 3/2006 | Gross |
| 2007/0078401 A1 | | 4/2007 | Servoss |
| 2007/0078439 A1 | * | 4/2007 | Grandt .................. A61M 25/10 604/523 |
| 2007/0106229 A1 | | 5/2007 | Wong |
| 2008/0097406 A1 | | 4/2008 | Freed |
| 2008/0306404 A1 | | 12/2008 | Ronald |
| 2008/0306465 A1 | * | 12/2008 | Bailey ............... A61M 25/0029 604/500 |
| 2009/0182260 A1 | | 7/2009 | Ronald |
| 2009/0318893 A1 | | 12/2009 | English |

OTHER PUBLICATIONS

Office Action dated Oct. 16, 2017 in related Canadian Patent Application No. 2,932,994.

Extended European Search Report dated Sep. 27, 2017 in related European Patent Application No. 11844593.1.

Office Action dated May 29, 2015 in Canadian Patent Application No. 2,855,066.

Office Action dated Jun. 7, 2018 in related European Patent Application No. 11844593.1.

* cited by examiner

MIXING SYSTEMS AND METHODS FOR RESEARCH, INDUSTRIAL AND MEDICAL USES

CROSS-REFERENCE TO RELATED APPLICATIONS

This application is a divisional of and claims priority to U.S. patent application Ser. No. 14/623,029, filed Feb. 16, 2015, which is a continuation of and claims priority to U.S. patent application Ser. No. 12/960,375, filed Dec. 3, 2010 and issued Mar. 3, 2015 as U.S. Pat. No. 8,968,238, each of which is hereby incorporated by reference in its entirety.

FIELD

The present disclosure relates to mixing systems and methods for chemicals, fluids, medications and other materials, including intravenous fluid delivery systems and methods.

BACKGROUND

In various industrial, laboratory and medical applications the ability to combine different chemicals, fluids, medications and other materials in compliance with strict sequence and timing parameters can be critical to success. More particularly, these materials must be kept separate from each other at certain times and be combined at certain times to be effective. In the construction industry, for example, careful attention must be paid to when water is added to cement or concrete mix so the material does not dry before it can be used. Wet laboratory research also requires that chemicals be added and removed at precise times to optimize reactions and avoid degradation of materials.

In medical care, especially in hospital operating rooms, recovery rooms and intensive care units, it is often necessary to deliver multiple medications, fluids and other nutrient materials concurrently to patients via intravenous (IV) infusion. These infusions may need to be kept separate, combined or changed quickly in dose and/or rate. The efficiency with which these infusions can be altered can often have profound implications on their efficacy and for the safety of the patient.

In existing IV tubing systems, dose and rate changes are accomplished through the use of multiple separate sets of IV tubing connected at a distance from the patient to IV fluid/medication bags and/or infusion pumps. If multiple medications and fluids have to be administered through fewer IV access points on the patient, they often are connected via stopcocks that allow multiple lines to be fed into a single carrier line, sometimes at a significant distance from the patient.

These existing approaches have significant drawbacks, which can lead to grave errors and inefficiencies that compromise the safety of the patient. Multiple IV lines can cause logistical difficulties such as tangled, knotted or disconnected IV lines. Caretakers' efforts to resolve these logistical complications often require multiple disconnections and re-connections of tubing, which leads to increased risk of infection and errors during re-connection of similar looking IV lines. The inadvertent connection of the wrong tube containing the wrong materials to the patient's vein can be extremely dangerous and fatal in some cases.

Another disadvantage is that there is a delay in changes made to the rate of administration of the medication because existing IV tubing systems feed the extra lines into the carrier line at a significant distance from the patient. In addition, boluses of fluid or medication may accumulate in the main carrier line, leading to excessive administration.

Therefore, there exists a need for a simpler system that allows greater control and facilitates precise mixing of chemicals, fluids, medications and other materials. There is also a need for a simpler and safer IV tubing system that allows administration of multiple medications and fluids without resort to multiple IV lines. There exists a need for an IV tubing system that facilitates control and precise regulation of the combination of the different medications and fluids at a point close to patients.

SUMMARY

The present disclosure, in its many embodiments, alleviates to a great extent the disadvantages of known mixing systems by providing a system of coaxial tubing in a single unit having a main carrier line and one or more administration lines that run along the outer length of the carrier line and join the main carrier line just before its distal connection point. The disclosed systems and methods advantageously provide the simplicity and efficiency of multiple lines in a single unit and the exacting control necessary to maintain different chemicals, fluids or medications separately while facilitating mixing at a point close to the distal end of the system.

Exemplary embodiments include a mixing device comprising a primary tube having a proximal end, a distal end, an outer surface and an inner lumen and at least one secondary tube having a proximal end, a distal end, an outer surface and an inner lumen. The at least one secondary tube runs substantially parallel to the primary tube, and the distal end of the at least one secondary tube is fluidly connected to the primary tube at a junction. The junction may be located on the primary tube close to the distal end of the primary tube. In exemplary embodiments, the primary tube and the at least one secondary tube have separate and distinct entry points at their proximal ends. The mixing device may comprise a back-flow prevention mechanism coupled thereto to maintain unidirectional flow of materials, and may also have a connector apparatus attached to the distal end of the primary tube.

In exemplary embodiments, the at least one secondary tube may comprise a plurality of secondary tubes, and at least one of the plurality of secondary tubes may be attached to the outer surface of the primary tube and extend longitudinally along the outer surface of the primary tube. In exemplary embodiments, at least one of the plurality of secondary tubes can peel away from the primary tube at or near the proximal end of the secondary tube, and the proximal end of the secondary tube comprises a port. The mixing device may also include at least one tertiary tube having a proximal end and a distal end, the at least one tertiary tube being substantially parallel to the primary tube and the secondary tube. The distal end of the at least one tertiary tube may have a separate and distinct exit point from an exit point of the primary tube.

In exemplary embodiments, the at least one primary tube and at least one secondary tube are in a co-axial arrangement with one tube running within the other. One or more of the primary tube and the at least one secondary tube may be color-coded to easily distinguish the different tubes. Further, one or more of the primary tube and the at least one secondary tube may be made of a low absorption material for more effective delivery of medications that are absorbed by standard tubing material or a low compliance material that allows for pressure transduction or measurement of other physiologic parameters such as arterial blood pressure monitoring.

In exemplary embodiments, an intravenous fluid delivery system is provided comprising at least one carrier line having a proximal end, a distal end, an outer surface and an inner lumen and at least one administration line having a proximal end, a distal end, an outer surface and an inner lumen. The at least one administration line runs substantially parallel to the at least one carrier line, and the distal end of the at least one administration line is fluidly connected to the at least one carrier line at a junction. The junction may be located on the at least one carrier line close to but spaced from the distal end of the at least one carrier line. In exemplary embodiments, the at least one carrier line and the at least one administration line have separate and distinct fluid entry ports at their proximal ends.

In exemplary embodiments, the at least one administration line comprises a plurality of administration lines. At least one of the plurality of administration lines may be attached to the outer surface of the at least one carrier line and extend longitudinally along the outer surface of the at least one carrier line. The at least one carrier line may comprise two or more bundled carrier lines, each carrier line having at least one associated administration line fluidly connected thereto. In exemplary embodiments, the distal end of the at least one secondary administration line may have a separate and distinct exit point from an exit point of the at least one carrier line such that a fluid traveling through the at least one secondary administration line does not mix with a fluid in the at least one carrier line.

The system may also include a connector apparatus attached to the distal end of the carrier line, the connector apparatus being configured to connect the carrier line to an intravenous fluid transfer component. Exemplary embodiments may further comprise an sealing clamp or occlusion clamp coupled to the at least one administration line at or near its distal end. One or more of the carrier line and the at least one administration line may be made of a low absorption material for more effective delivery of medications that are absorbed by standard tubing material or a low compliance material that allows for pressure transduction or measurement of other physiologic parameters such as arterial blood pressure monitoring.

Exemplary embodiments include a clamp assembly comprising an outer sheath having a proximal end, a distal end, an outer surface, an inner surface and defining an inner lumen, and an inner tube disposed within the inner lumen of the outer sheath and releasably coupled to the outer sheath. A first actuator is located at or near the distal end of the outer sheath, and a second actuator is located at or near the proximal end of the outer sheath. The clamp assembly may also comprise a retaining clip adjacent the first actuator. The inner tube has a top half portion and a bottom half portion, and each of the top half portion and the bottom half portion has a proximal end, a distal end, an outer surface and an inner surface. The top and bottom half portion of the inner tube define an inner lumen of the inner tube.

In exemplary embodiments, a first protrusion is formed on the inner surface of the top half portion of the inner tube at or near the distal end of the top half portion and substantially beneath the first actuator. Similarly, a second protrusion is formed on the inner surface of the bottom half portion at or near the distal end of the bottom half portion and substantially beneath the first protrusion. A first cutting element is formed on the inner surface of the top half portion of the inner tube at or near the proximal end of the top half portion and substantially beneath the second actuator. A second cutting element is formed on the inner surface of the bottom half portion of the inner tube at or near the proximal end of the bottom half portion and substantially beneath the first cutting element. When the first actuator is pressed, the first protrusion translates from an open position to a closed position such that the first protrusion and second protrusion seal the inner lumen of the inner tube in the closed position. When the second actuator is pressed, the first cutting element moves from an open position to a closed position toward the second cutting element in a cutting motion. In exemplary embodiments, the top half portion and a bottom half portion of the inner tube comprise a linking mechanism fixedly attaching the top half portion to the bottom half portion when the first protrusion is in the closed position.

Exemplary embodiments include a method of mixing materials comprising directing a first material through at least one main passageway such that the material travels in a first direction and directing a second material through at least one secondary passageway such that the second material travels in substantially the same direction as the first material. Each of the at least one main passageway and the at least one secondary passageway has a proximal end and a distal end.

The second material is directed through a junction fluidly connecting the at least one secondary passageway to the at least one primary passageway such that the first material and second material are combined at a point close to but spaced from the distal end of the at least one primary passageway. A third material may be directed through a tertiary passageway such that the third material travels in substantially the same direction as the first material and second material. The third material may be directed through an exit point of the tertiary passageway separate and distinct from an exit point of the main passageway such that the third material does not mix with the first material and second material.

Accordingly, it is seen that mixing devices are provided which allow simpler, safer and more precise mixing of chemicals, fluids, medications and other materials. These and other features of the present invention will be appreciated from review of the following detailed description of the invention, along with the accompanying figures in which like reference numbers refer to like parts throughout.

BRIEF DESCRIPTION OF THE DRAWINGS

The foregoing and other objects of the disclosure will be apparent upon consideration of the following detailed description, taken in conjunction with the accompanying drawings, in which:

FIG. 18C-2 is a cross-sectional view of the distal end of the mixing device of FIG. 18A;

FIG. 19A-1 is a perspective view of a proximal end of an embodiment of a mixing device in accordance with the present disclosure;

FIG. 19A-2 is a perspective view of a distal end of an embodiment of a mixing device in accordance with the present disclosure;

FIG. 19B-1 is a cross-sectional view of the proximal end of the mixing device of FIGS. 19A-1 and 19A-2;

FIG. 19B-2 is a cross-sectional view of the distal end of the mixing device of FIGS. 19A-1 and 19A-2;

DETAILED DESCRIPTION

Figure 1A:
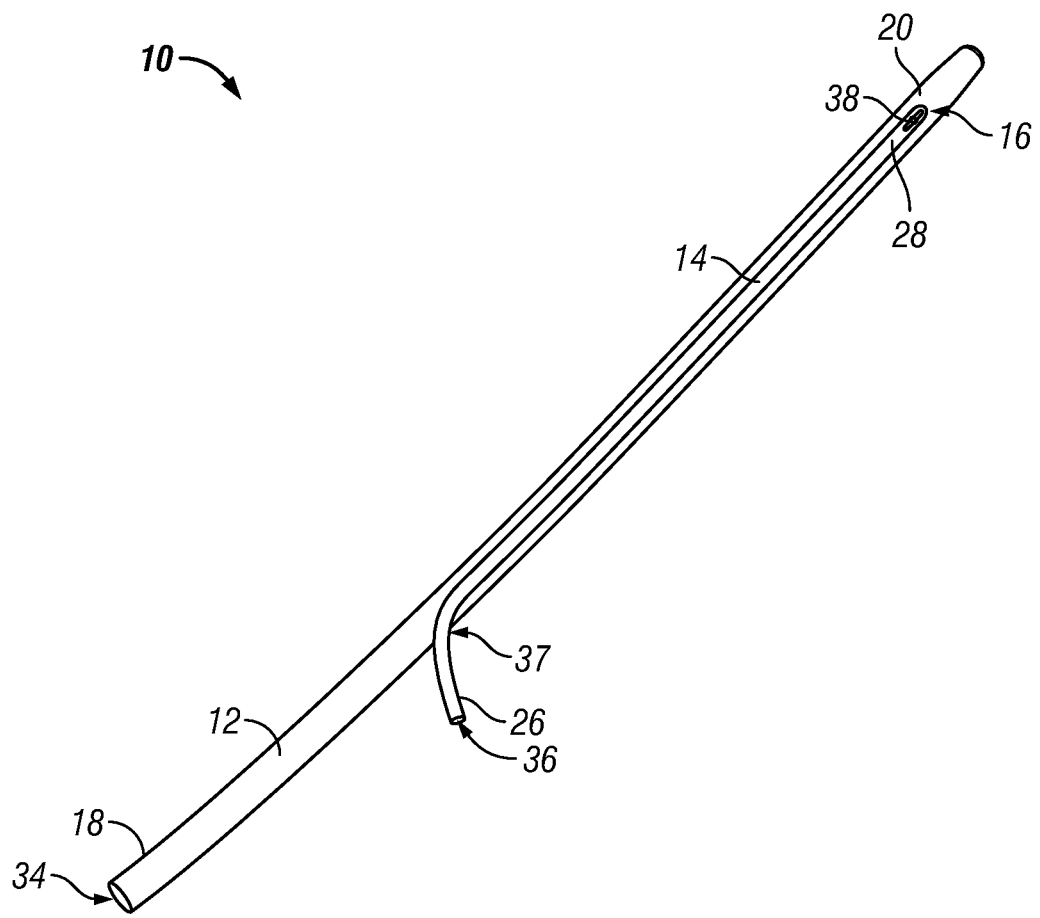
FIG. 1A is a perspective view of an embodiment of a mixing device in accordance with the present disclosure.
Figure 1B:
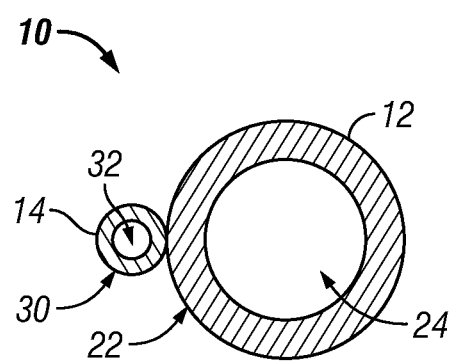
FIG. 1B is a cross-sectional view of the mixing device of FIG. 1A.
Figure 1C:
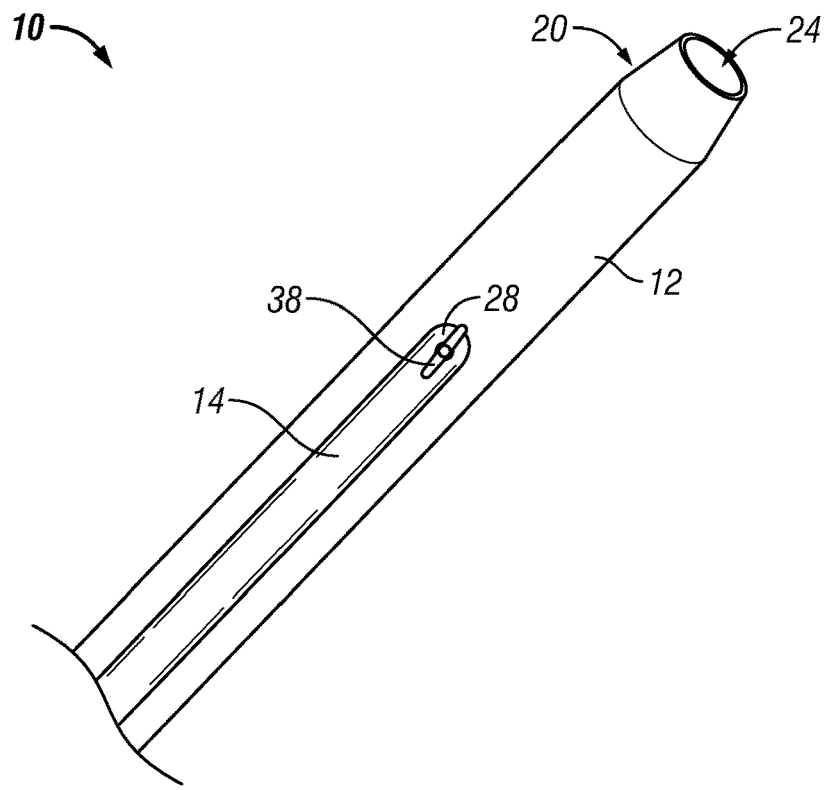
FIG. 1C is a perspective view of a distal end of the mixing device of FIG. 1A.
Figure 1D:
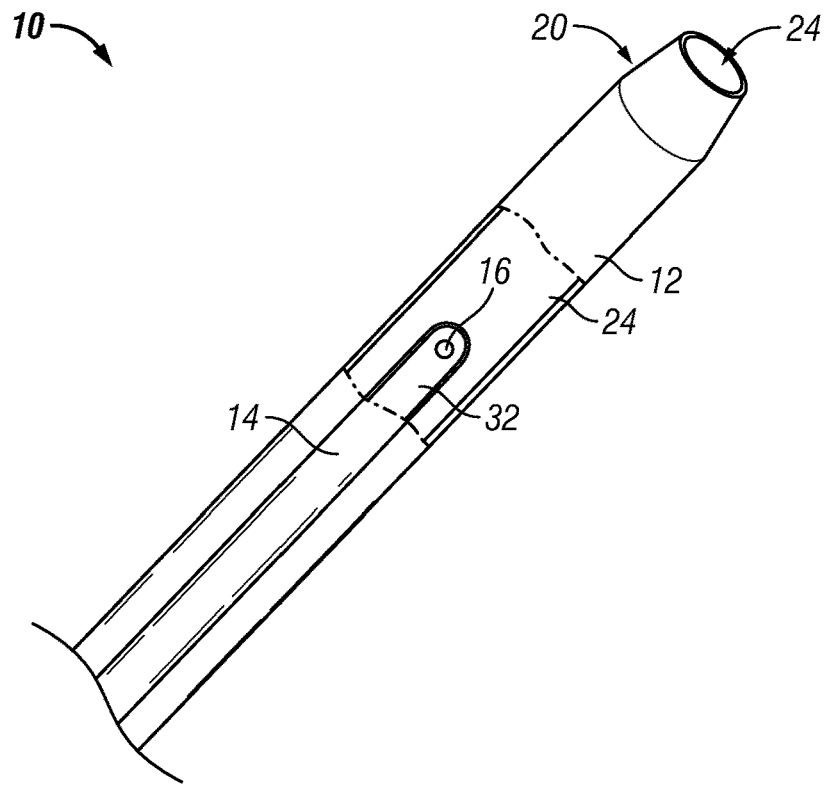
FIG. 1D is a cutaway view of a distal end of the mixing device of FIG. 1A.
Figure 1E:
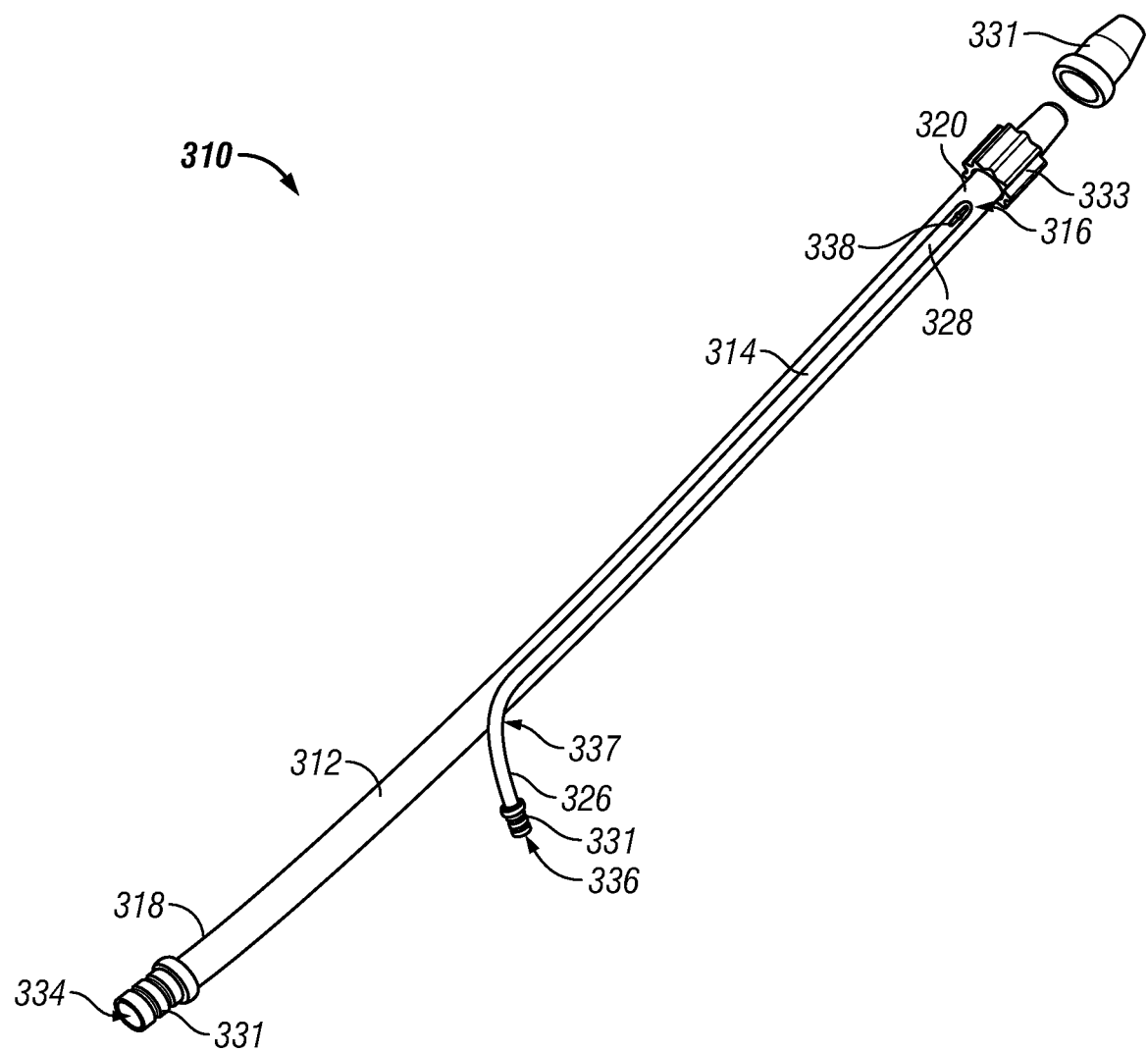
FIG. 1E is a perspective view of an embodiment of an intravenous fluid delivery system in accordance with the present disclosure.

In the following paragraphs, embodiments will be described in detail by way of example with reference to the accompanying drawings, which are not drawn to scale, and the illustrated components are not necessarily drawn proportionately to one another. Throughout this description, the embodiments and examples shown should be considered as exemplars, rather than as limitations of the present disclosure. As used herein, the "present disclosure" refers to any one of the embodiments described herein, and any equivalents. Furthermore, reference to various aspects of the disclosure throughout this document does not mean that all claimed embodiments or methods must include the referenced aspects. Reference to temperature, pressure, density and other parameters should be considered as representative and illustrative of the capabilities of exemplary embodiments, and embodiments can operate with a wide variety of such parameters. It should be noted that the figures do not show every piece of equipment, nor the pressures, temperatures and flow rates of the various streams.

Exemplary embodiments of a mixing device will be described with reference to FIGS. 1A-D, 2A-D, 3A-D, 4A-D and 20A-E. Mixing device 10 can be used in any application in which various materials need to be combined with precision and advantageously allows precise control over the timing and sequence of mixing the materials. In exemplary embodiments, a mixing device 10 includes a primary tube 12 and at least one secondary tube 14 fluidly connected to the primary tube at a junction 16. The primary tube 12 has a proximal end 18, a distal end 20, an outer surface 22 and defines an inner lumen 24. Similarly, the secondary tube has a proximal end 26, a distal end 28, an outer surface 30 and defines an inner lumen 32. The primary tube 12 has an entry point 34, which could be any type of port for introducing fluid or materials, at its proximal end 26, and the secondary tube 14 has a distinct entry point 36 at its proximal end 26. The secondary tubes 14 may have a bend or kink 37 to facilitate access of materials into entry point 36.

The length, thickness and diameters of the primary and secondary tubes may vary depending on the application, and in exemplary embodiments the diameter of the secondary tube 14 is relatively smaller than the diameter of the primary tube 12. With reference to FIGS. 18A-19B, it should be noted that any variation of primary and secondary tubes could be used, and all the tubes could have substantially the same diameter. Thus, a mixing device 410 may comprise four secondary tubes 414 coupled together that converge into a primary tube 412 at or near the distal end of the 420 of the primary tube 412. Alternatively, the mixing device 610 may comprise a single tube subdivided into four secondary tubes 614 that converge into an undivided primary tube 612 at or near its distal end 620.

Figure 2A:
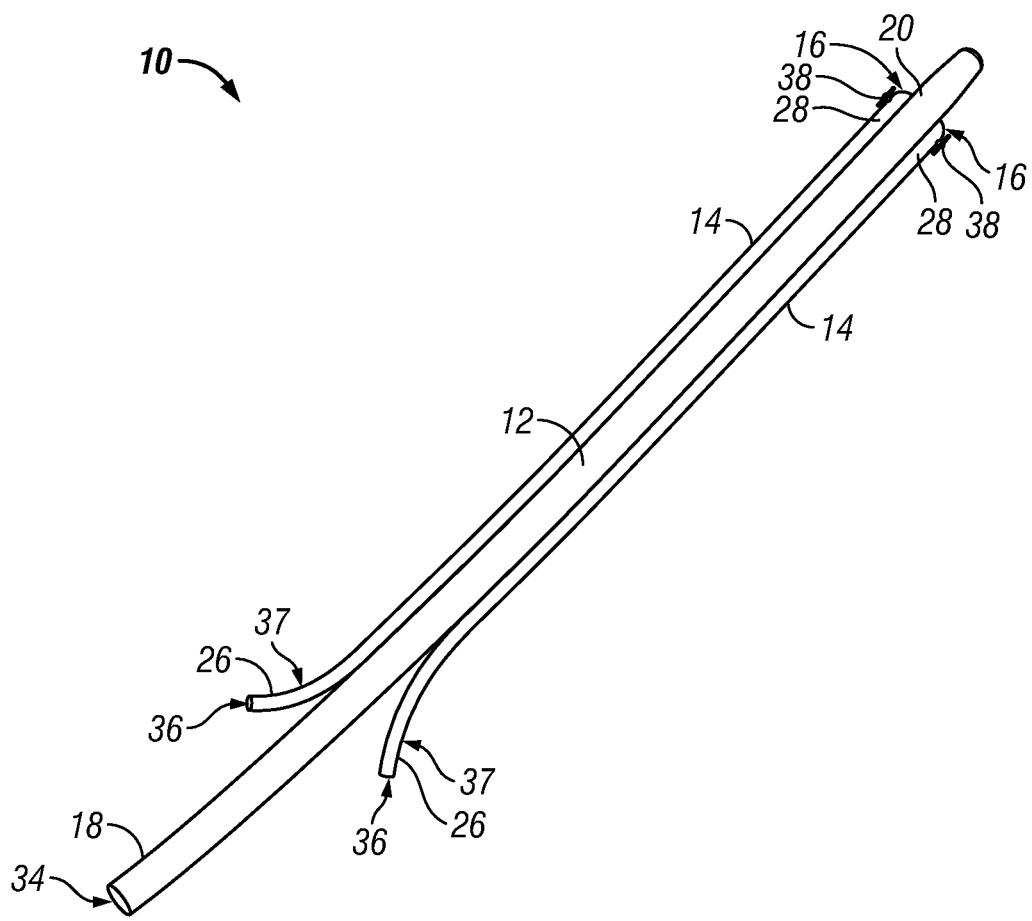
FIG. 2A is a perspective view of an embodiment of a mixing device in accordance with the present disclosure.
Figure 2B:
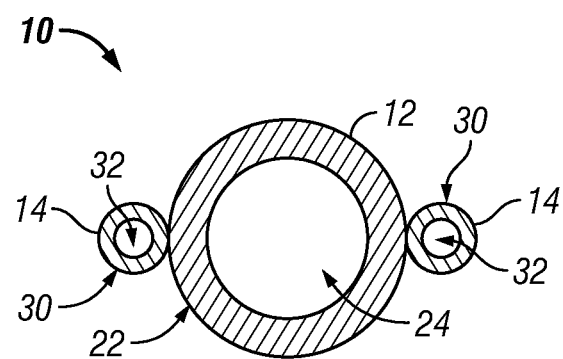
FIG. 2B is a cross-sectional view of an embodiment the mixing device of FIG. 2A.
Figure 2C:
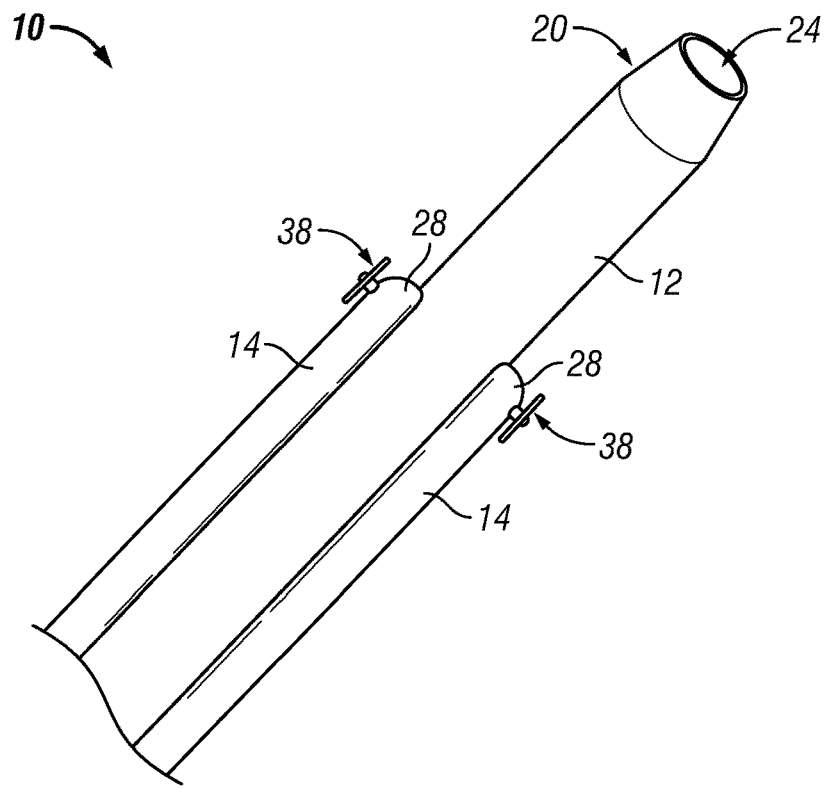
FIG. 2C is a perspective view of a distal end of the mixing device of FIG. 2A.
Figure 2D:
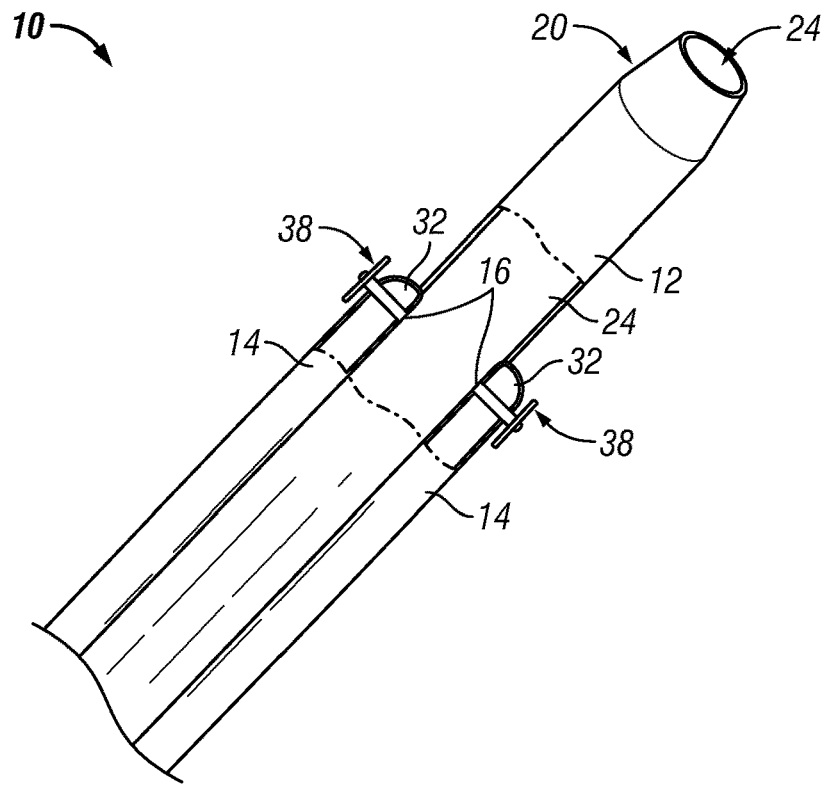
FIG. 2D is a cutaway view of a distal end of the mixing device of FIG. 2A.
Figure 2E:
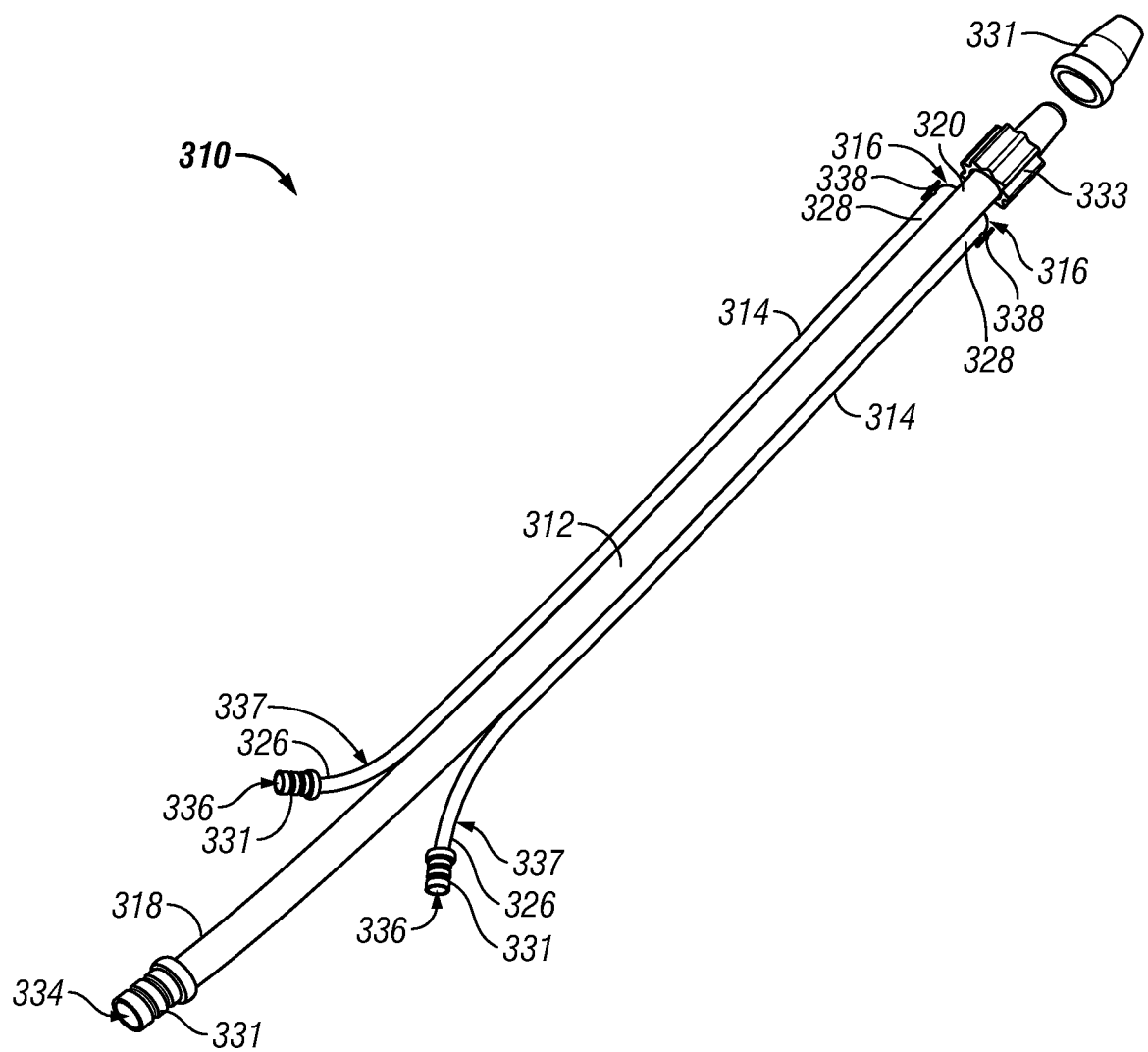
FIG. 2E is a perspective view of an embodiment of an intravenous fluid delivery system in accordance with the present disclosure.
Figure 3A:
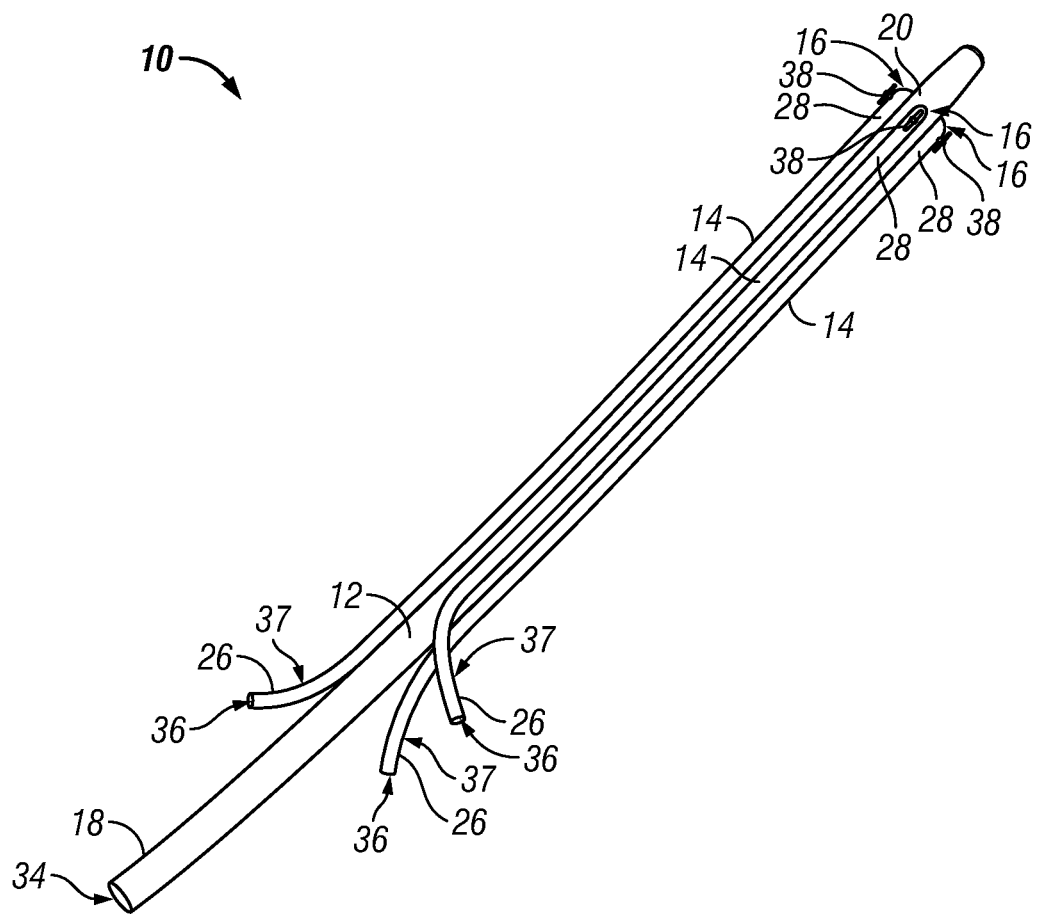
FIG. 3A is a perspective view of an embodiment of a mixing device in accordance with the present disclosure.
Figure 3B:
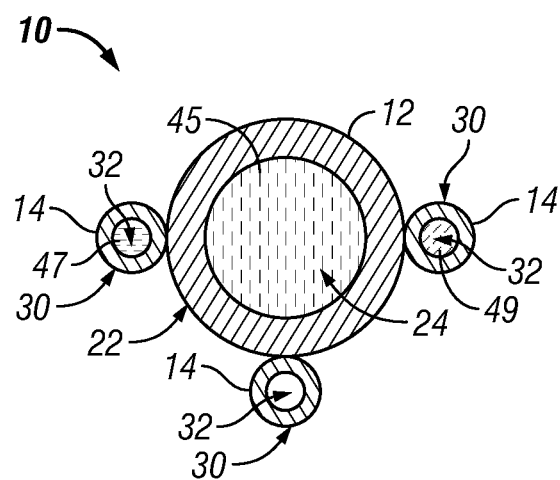
FIG. 3B is a cross-sectional view of the mixing device of FIG. 3A.
Figure 3C:
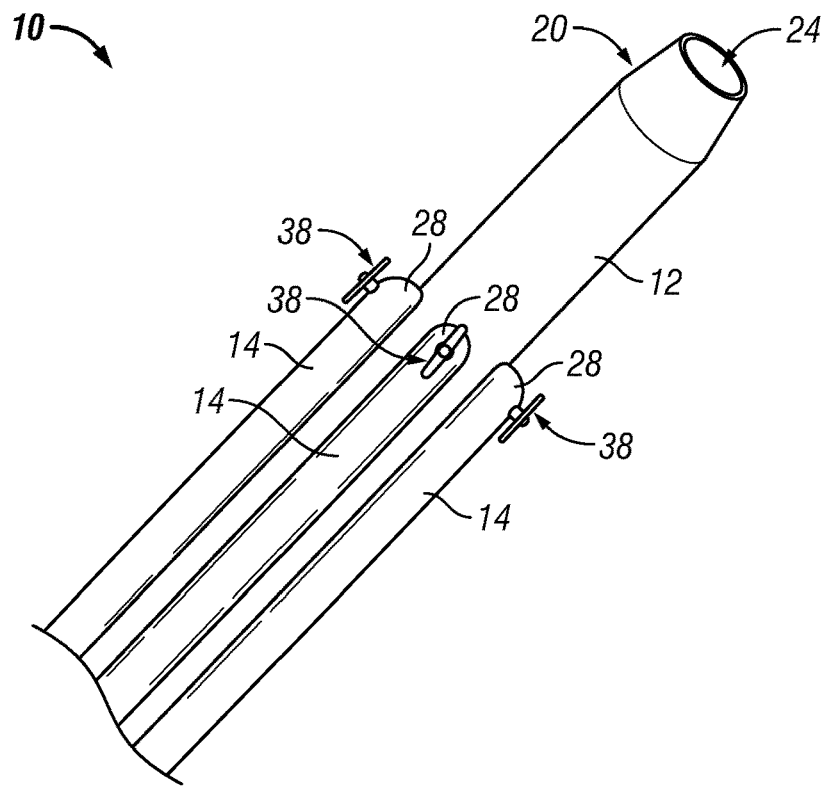
FIG. 3C is a perspective view of a distal end of the mixing device of FIG. 3A.
Figure 3D:
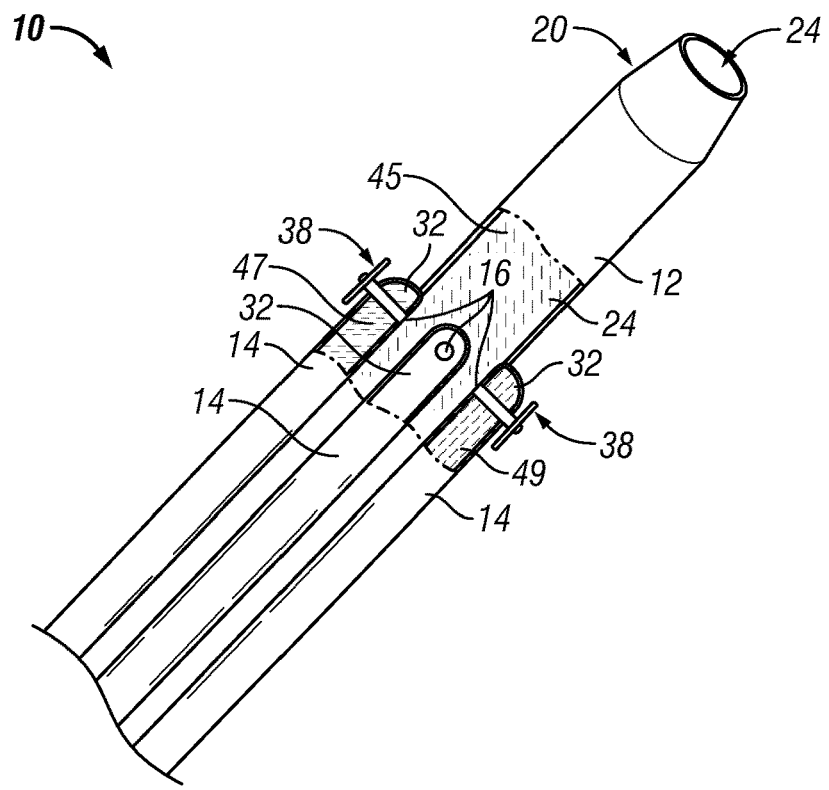
FIG. 3D is a cutaway view of a distal end of the mixing device of FIG. 3A.
Figure 3E:
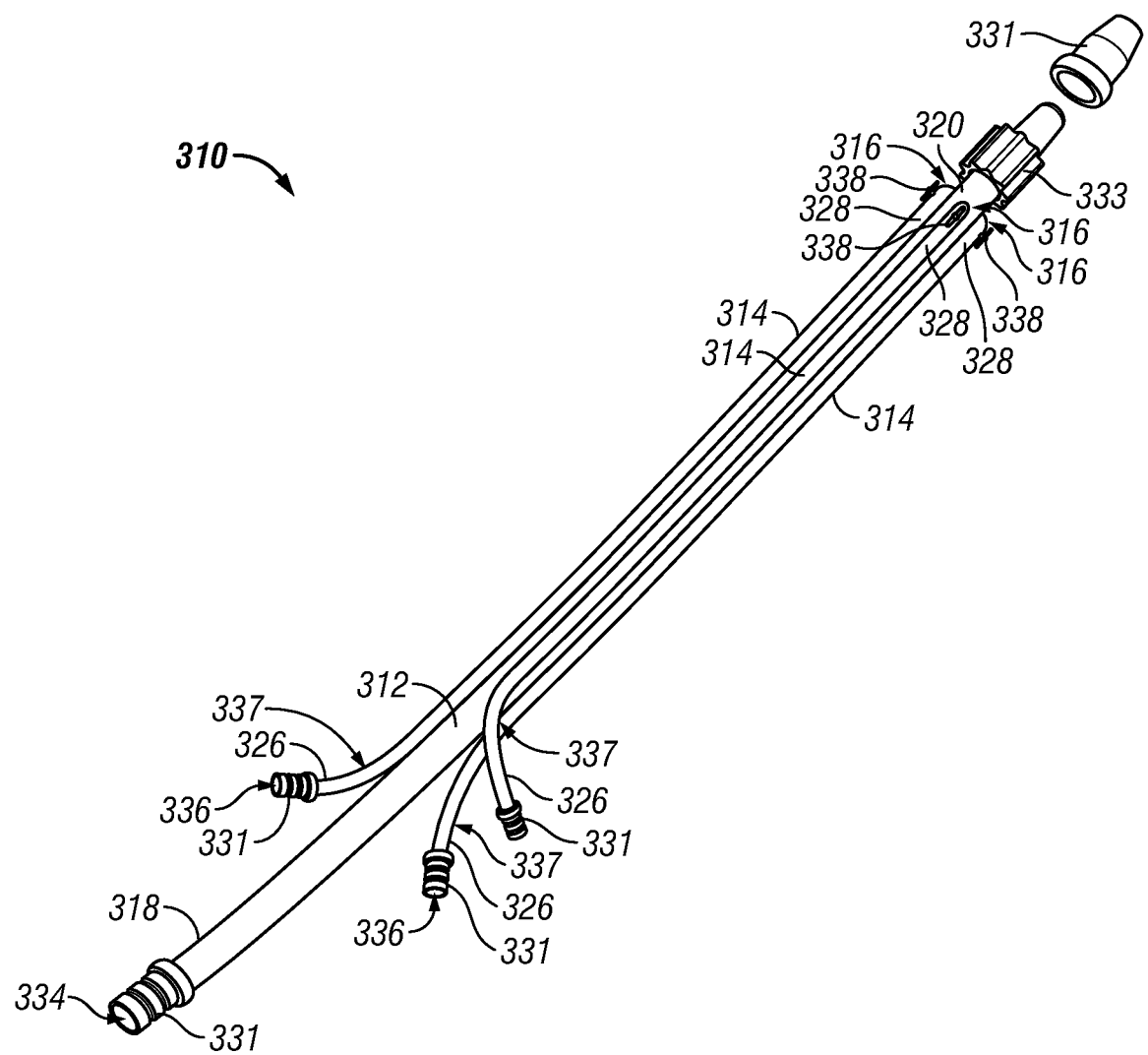
FIG. 3E is a perspective view of an embodiment of an intravenous fluid delivery system in accordance with the present disclosure.
Figures 4A, 4B:
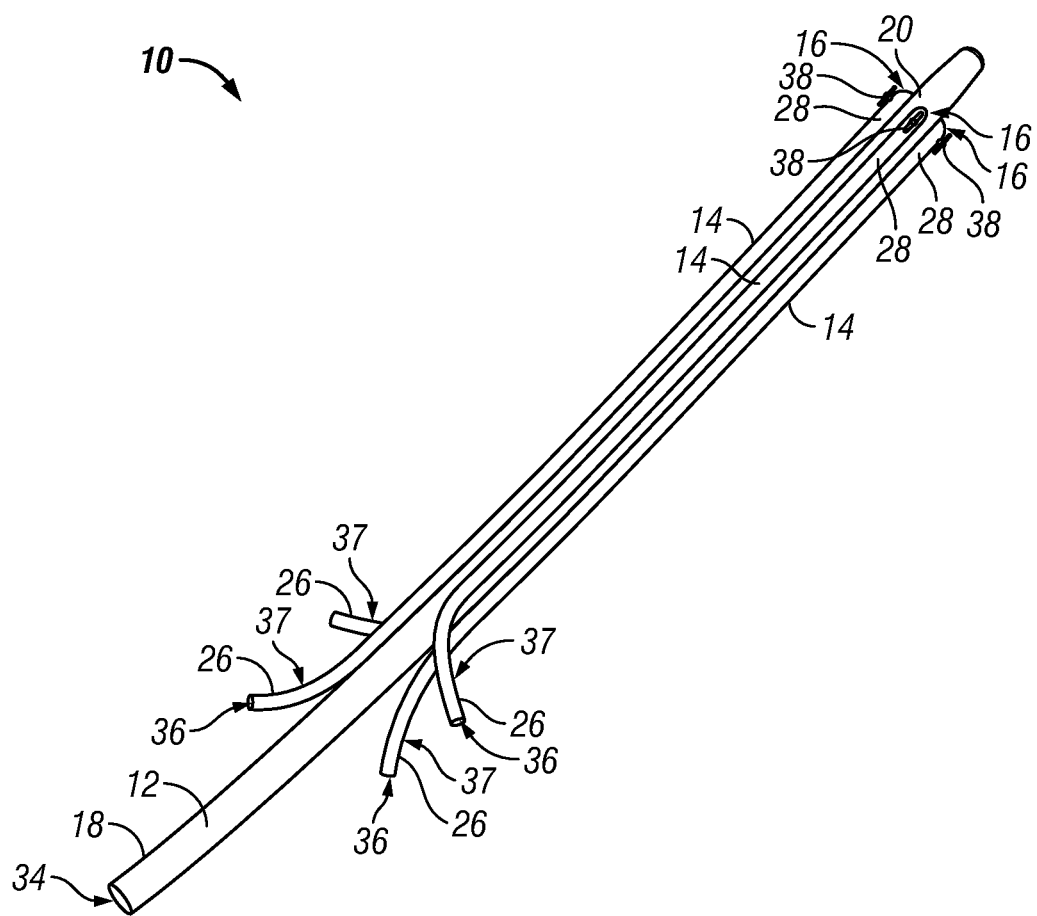
FIG. 4A is a perspective view of an embodiment of a mixing device in accordance with the present disclosure.
FIG. 4B is a cross-sectional view of the mixing device of FIG. 4A.
Figure 4C:
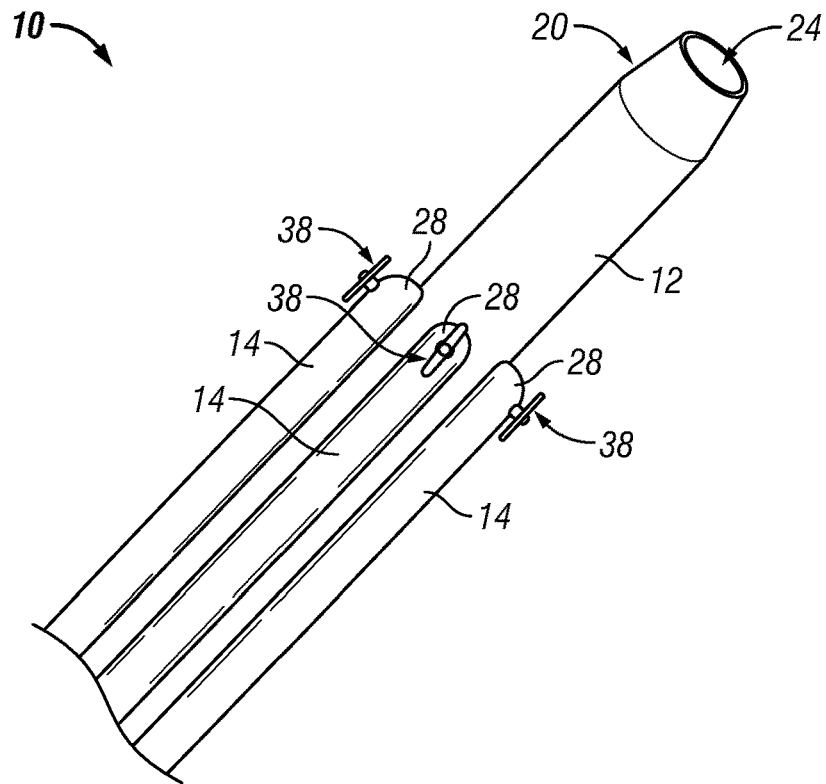
FIG. 4C is a perspective view of a distal end of the mixing device of FIG. 4A.
Figure 4D:
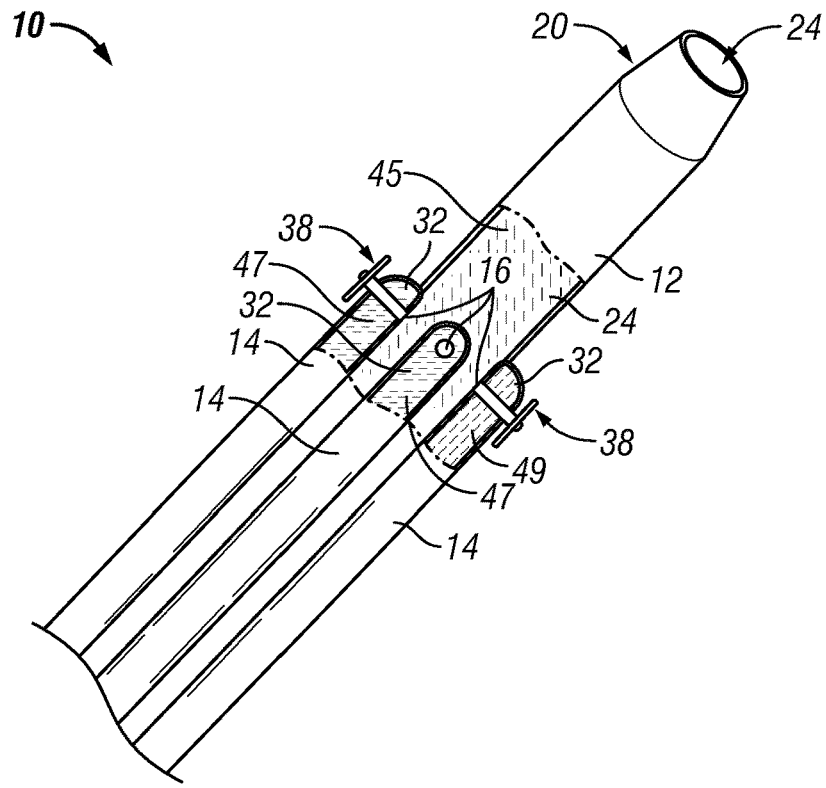
FIG. 4D is a cutaway view of a distal end of the mixing device of FIG. 4A.
Figure 4E:
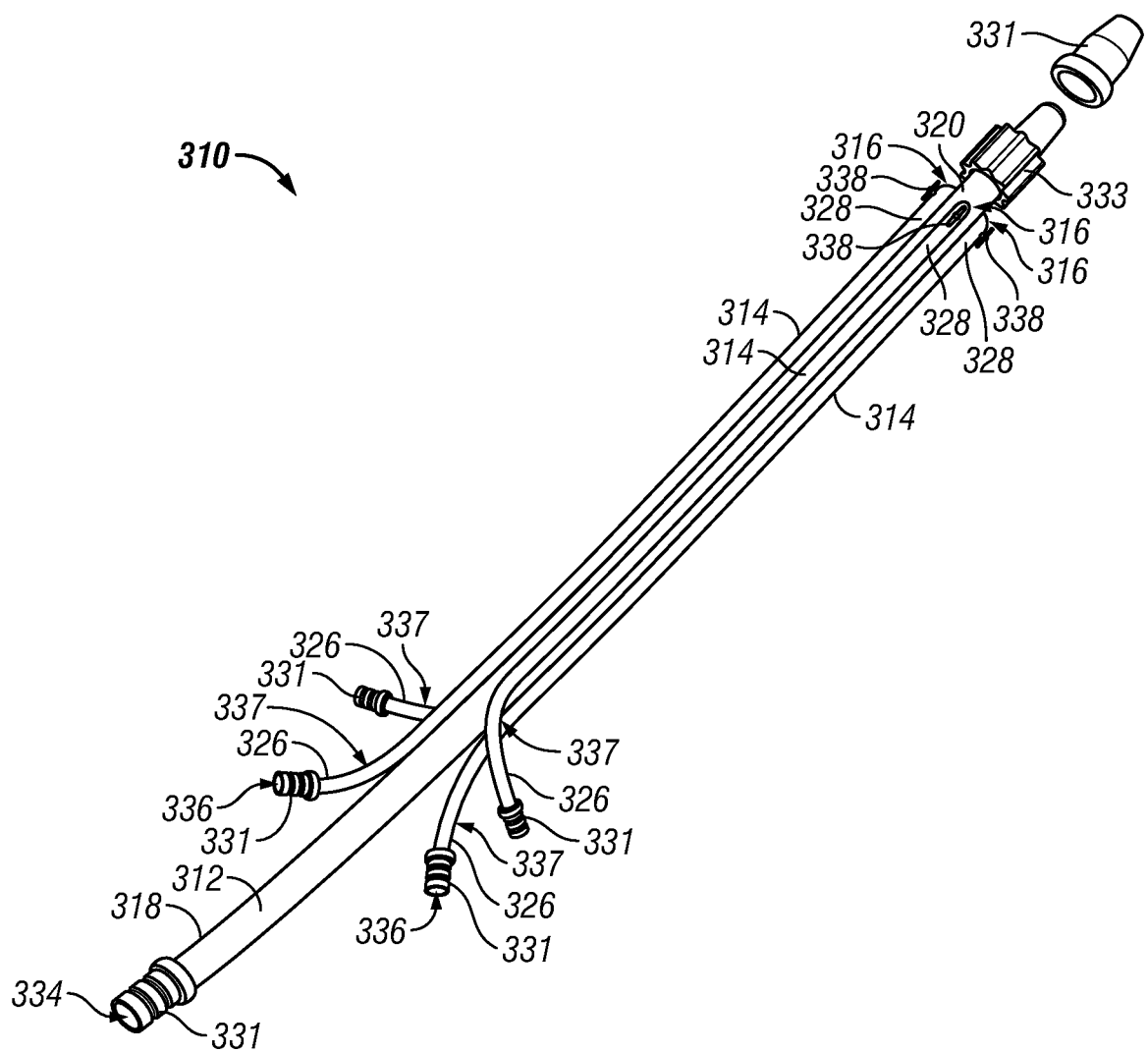
FIG. 4E is a perspective view of an embodiment of an intravenous fluid delivery system in accordance with the present disclosure.

The secondary tube 14 runs substantially parallel to the primary tube 12, and in most uses fluids or other materials traveling through the primary and secondary tubes 12, 14 flow in the same direction. The secondary tube 14 may be attached to the outer surface 22 of the primary tube 12. As best seen in FIGS. 2B, 3B and 4B, multiple secondary tubes 14 may be spaced from each other around the outer surface 22 of the primary tube 12. In exemplary embodiments, the secondary tube 14 extends longitudinally along the outer surface 22 of the primary tube 12, and may be attached at one or more attachment points or have a continuous attachment along much of the length of the outer surface of the primary tube 12 and secondary tube 14.

The attachment of the primary and secondary tubes advantageously makes the mixing device efficient and easy to use by providing a compact, uniform design with the tubes attached in a single unit. As discussed in more detail herein, one or more secondary tubes 14 may be removably attached to the primary tube 12 so they can be peeled away or detached from the primary tube 12 and discarded after the secondary tube has been used. The detachment of one or more secondary tubes may be facilitated by severing the tubes using a cutting mechanism of a clamp assembly, as discussed in more detail herein.

As best seen in FIGS. 1D, 2D, 3D and 4D, junction 16 is located on the primary tube 12 close to its distal end 20. In exemplary embodiments, the junction 16 provides a fluid connection between at least one secondary tube 14 and the primary tube 12 so a fluid or other material flowing through the secondary tube 14 combines with a different fluid or material flowing through the primary tube 12. Each junction 16 is spaced slightly proximal of the distal end 20 of the primary tube 12 so the fluids or other materials from one or more secondary tubes 14 can enter the primary tube 12 and combine with the fluid or material in the primary tube 12 before the combined materials exit the distal end 20 of the primary tube 12. The junction 16 should be close enough to the distal end 20 of the primary tube 12 to optimize or substantially reduce the amount of the time for which a change in materials, chemicals, or medication, or a change in amount or dosage of the materials, chemicals, or medication administered by the user is reflected in the materials, chemicals, or medication exiting the distal end 20 of the primary tube 12. This distance of the junction 16 from the distal end 20 of the primary tube 12 could vary considerably depending on the particular use of the mixing device, and may be between about 1 mm and 25 cm.

As shown in FIGS. 20A-20E, a proximal portion of each secondary tube 14 may extend longitudinally along the outer surface 22 of the primary tube 12, and a distal portion of each secondary tube 14 may extend longitudinally along the inner surface 23 of the primary tube 12. More particularly, each secondary tube 14 extends along the outer surface 22 of the primary tube 12 until it reaches a cross-through point 13, at which each secondary tube 14 penetrates the outer surface 22 of the primary tube 12 and enters the inner lumen 24 of the primary tube 12. Each secondary tube 14 then extends along the inner surface 23 of the primary tube through the inner lumen 24 from the cross-through point 13 to a junction 16 near the distal end 20 of the primary tube 12. Each secondary tube 14 maintains a separate conduit and is fluidly connected with the primary tube 12 at a junction 16 located in the inner lumen 24 of the primary tube 12 at or near the distal end 20 of the primary tube 12. This configuration of much of the secondary tubes 14 within the primary tube 12 advantageously provides a more streamlined and compact design.

In exemplary embodiments shown in FIGS. 21A-21E, a portion of each secondary tube 14 may extend within the wall 11 of the primary tube 12. More particularly, each secondary tube 14 extends along the outer surface 22 of the primary tube 12 until it reaches a cross-through point 13, at which each secondary tube 14 penetrates the outer surface 22 of the primary tube 12 and enters the wall 11 of the primary tube 12. Each secondary tube 14 then extends through the wall 11 of the primary tube from the cross-through point 13 to the distal end 20 of the primary tube 12. Each secondary tube 14 is fluidly connected with the inner lumen 24 of the primary tube 12 at a junction 16 located at or near the distal end 20 of the primary tube 12. This configuration of much of the secondary tubes 14 within the wall 11 of the primary tube 12 advantageously provides a more streamlined and compact design while allowing the full inner lumen 24 of the primary tube 12 to remain open for flow of a primary material, chemical or medication 45.

This controlled convergence of fluids from one or more secondary tubes to a primary tube near the distal end of the primary tube advantageously provides the ability to transport multiple different materials individually, then mix them with precise volumes and timing and finally transport the combined materials together out of the distal end 20 of the primary tube 12. The distal end 20 of the primary tube 12 could have any kind of connector apparatus attached thereto to fluidly connect the primary tube 12 to other tubing, industrial or scientific apparatus or intravenous delivery tubing or apparatus for delivering medication to human beings or animals undergoing medical care.

Figure 5:
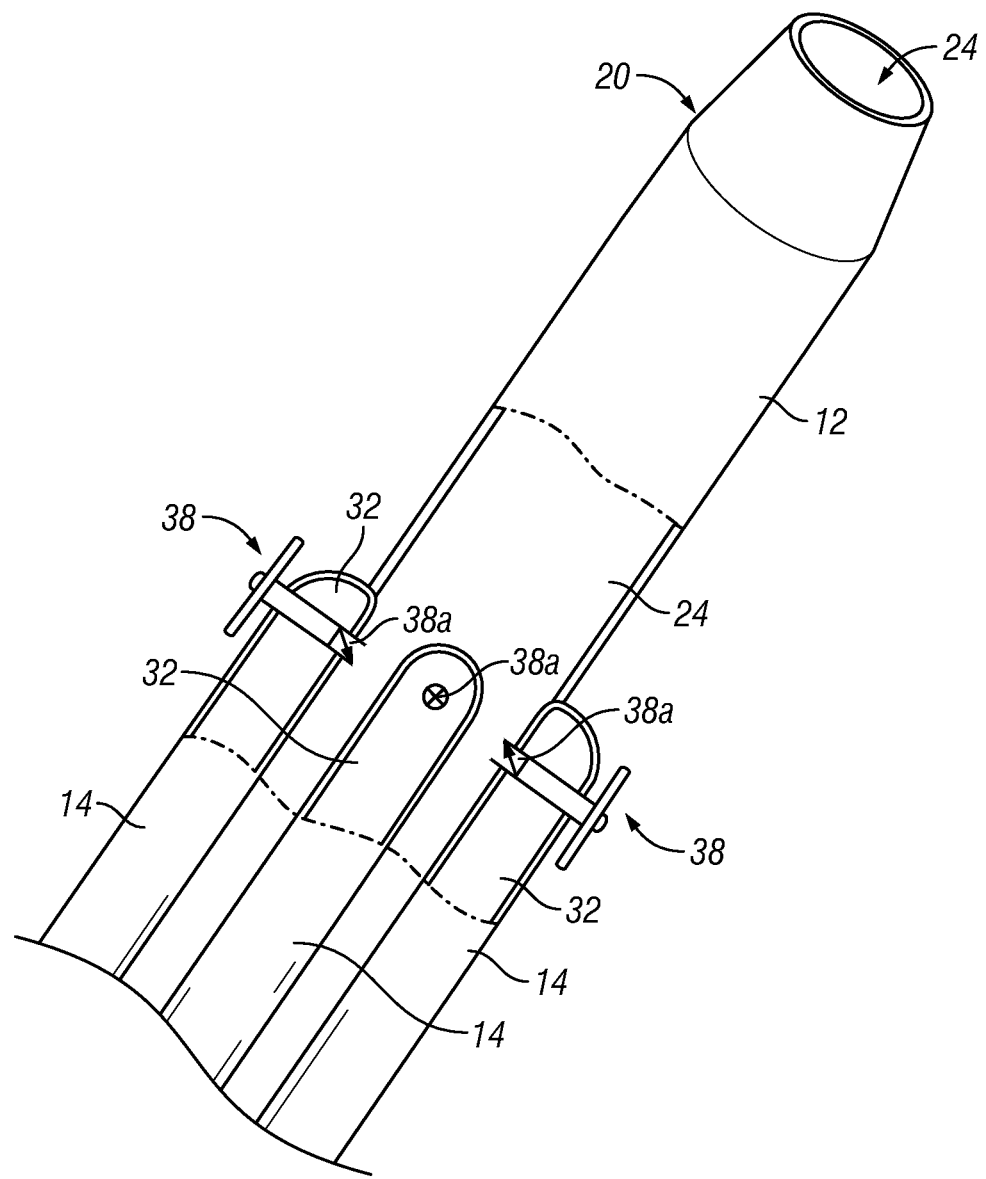
FIG. 5 is a detail cutaway view of a distal end of an embodiment of a mixing device in accordance with the present disclosure.
Figure 6:
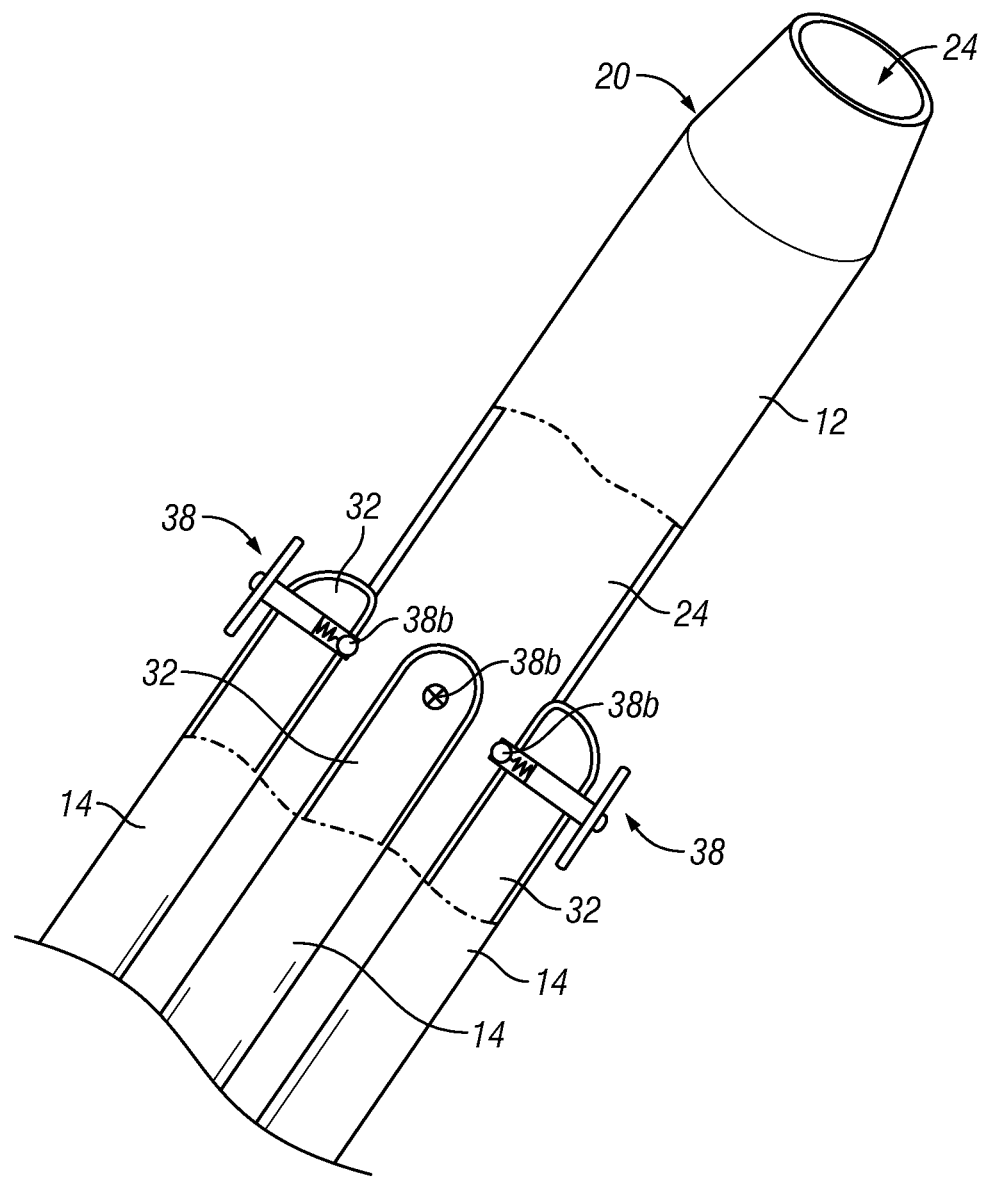
FIG. 6 is a detail cutaway view of a distal end of an embodiment of a mixing device in accordance with the present disclosure.
Figure 7A:
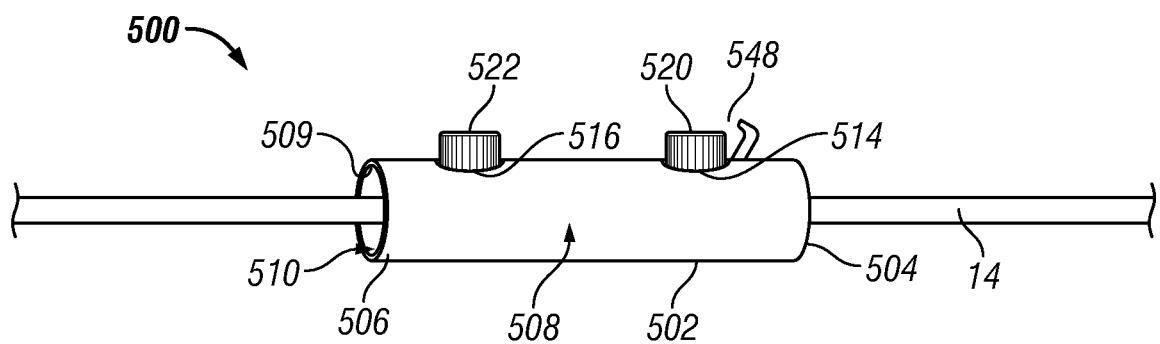
FIG. 7A is a perspective view of an embodiment of a clamp assembly in accordance with the present disclosure.
Figure 7B:
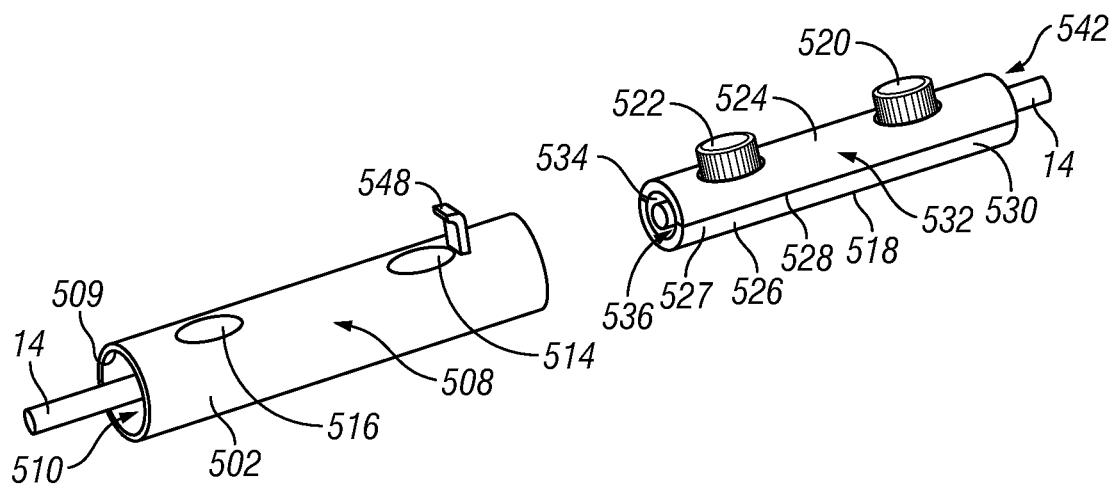
FIG. 7B is a perspective view of an embodiment of a clamp assembly in accordance with the present disclosure.
Figure 8A:
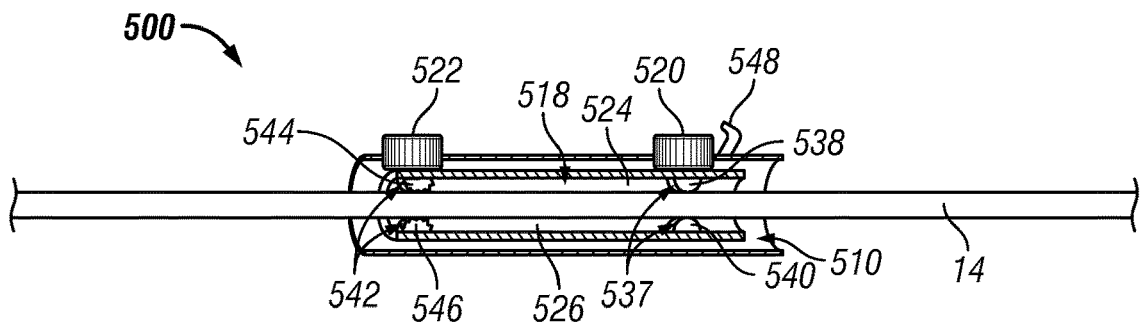
FIG. 8A is a side cutaway view of an embodiment of clamp assembly in an open position in accordance with the present disclosure.
Figure 8B:
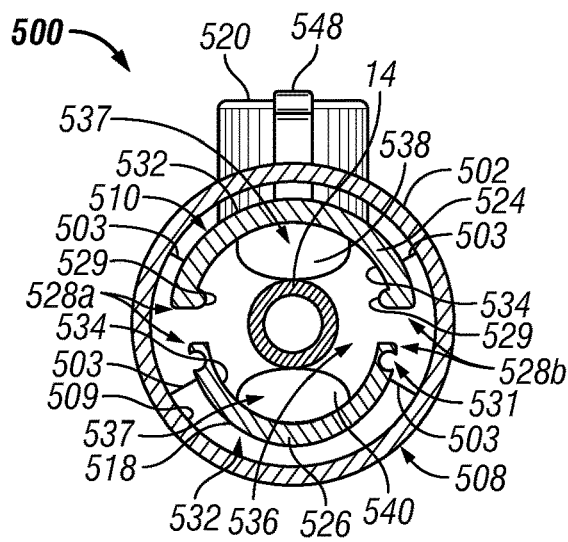
FIG. 8B is a cross-sectional view of a distal end of an embodiment of a clamp assembly shown in an open position in accordance with the present disclosure.
Figure 8C:
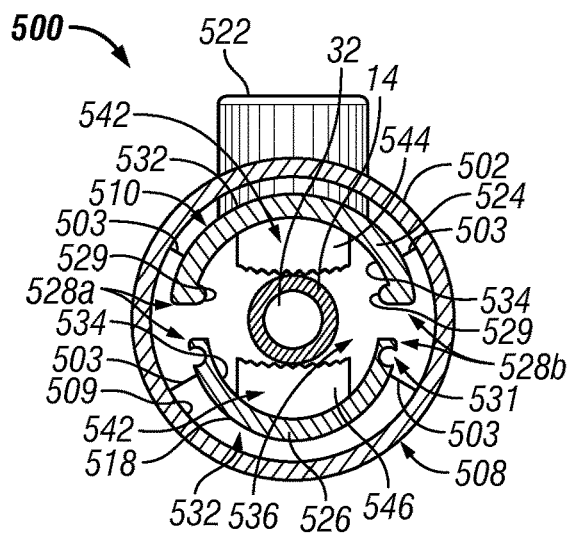
FIG. 8C is a cross-sectional view of a proximal end of an embodiment of a clamp assembly shown in an open position in accordance with the present disclosure.

Referring to FIGS. 5 and 6, exemplary embodiments of a mixing device 10 may comprise additional components to regulate and control the flow of materials from the secondary tubes 14 to the primary tube 12. For example, one or more of the secondary tubes 14 could be equipped with a mechanism to prevent back-flow of the fluid or material from the primary tube 12 into the secondary tube 14. Such a back-flow mechanism 38 may be coupled to the secondary tube 14 at its distal end 20 at or near junction 16. The back-flow mechanism 38 could employ any variety of clamp, one-way check valve 38a, ball valve 38b, or any other device that would regulate material flow and prevent material from leaking backwards from the primary tube 12 to a secondary tube 14. The back-flow mechanism 38 could be located at other points along the secondary tube 14 if desired, such as halfway along the length of the secondary tube 14 or at or near its proximal end 26. Similarly, as discussed in more detail herein, the mixing device 10 could have an occlusion clamp 500 coupled to the secondary tube 14 to seal the tube and prevent material from passing through junction 16 to primary tube 12.

With reference to FIGS. 7A-10B, exemplary embodiments of a sealing clamp, or occlusion clamp, will now be described. An exemplary embodiment of a clamp assembly 500 has a co-axial dual tube structure so it can be threaded over a primary, secondary or tertiary tube, as described in more detail herein. More particularly, the clamp assembly 500 may comprise an outer sheath 502 that has a proximal end 504, a distal end 506, an outer surface 508, an inner surface 509 and defines an inner lumen 510, and an inner tube 518 disposed within the inner lumen 510 of the outer sheath 502.

In exemplary embodiments, the inner tube 518 is a cylinder formed of a top half portion 524 and a bottom half portion 526. The top and bottom half portions 524, 526 are corresponding components, and each has a proximal end 527, a distal end 530, an outer surface 532 and an inner surface 534. Together, the top and bottom half portions 524, 526 define an inner lumen 536 of the inner tube 518. The top and bottom half portions 524, 526 are unconnected when in an open position and connected by connection portions 528a, 528b on either side of the inner tube 518 when in a closed position and the secondary tube 514 is cut and permanently sealed. The connection portions 528a, 528b may be composed of any type of connection mechanism that can fixedly attach the top and bottom half portions 524, 526 of the inner tube 518. In exemplary embodiments, each connection portion 528a, 528b comprises a male connecting portion 529 that may be integrally formed with the top half portion 524 of the inner tube 518 and a female connecting portion 531 defined by an end of the bottom half portion 524 of the inner tube 518. As described in more detail herein, the male and female connecting portions 529, 531 form a snap-fit to connect the top and bottom half portions 524, 526 of the inner tube 518 when in a closed position and the secondary tube 514 is cut and permanently sealed.

The inner tube 518 may be releasably coupled to the outer sheath 502 by a linking mechanism 503. The linking mechanism 503 may be anything that maintains a temporary attachment between the inner surface 509 of the outer sheath 502 and the outer surface 532 of the inner tube 518 such that the attachment can be easily broken by minimal force to manually separate the outer sheath 502 from the inner tube 518. In exemplary embodiments, linking mechanism 503 comprises a plurality of thin sheets of material such as plastic that maintain the temporary attachment between the inner surface 509 of the outer sheath 502 and the outer surface 532 of the inner tube 518 but sever easily.

A first actuator 520 may be located at or near the distal end 506 of the outer sheath 502, and a second actuator 522 may be located at or near the proximal end 504 of the sheath. In exemplary embodiments, the actuators 520, 522 are buttons or other mechanisms that may be easily depressed by the user. The outer sheath 502 may define one or more apertures 514, 516 to house the actuators. More particularly, the first actuator 520 may be partially disposed in a first aperture 514 located at or near the distal end 506 of the outer sheath 502 and the second actuator 522 may be partially disposed in a second aperture 516 located at or near the proximal end 504 of the outer sheath. It should be noted that the locations of the actuators 520, 522 could be located anywhere along the outer sheath 502 of the clamp assembly as long as one of the actuators engages the temporary clamping mechanism 537 and the other engages the cutting mechanism 542.

Figure 9A:
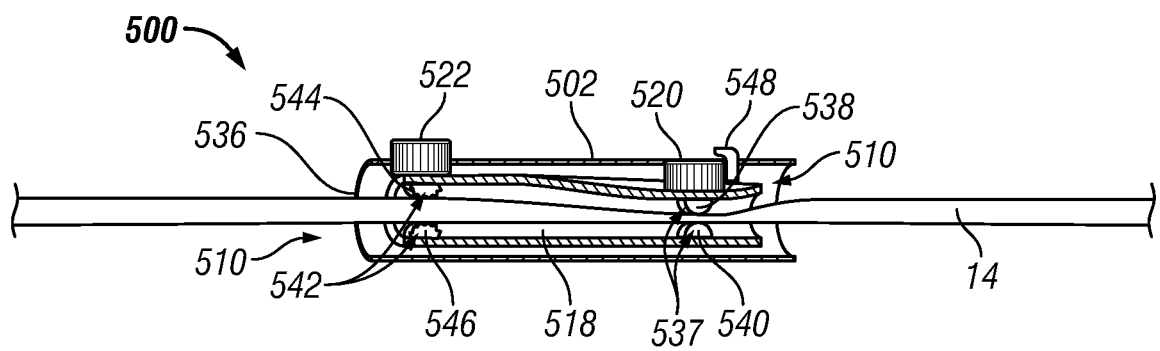
FIG. 9A is a side cutaway view of an embodiment of clamp assembly shown in a sealing configuration in accordance with the present disclosure.
Figure 9B:
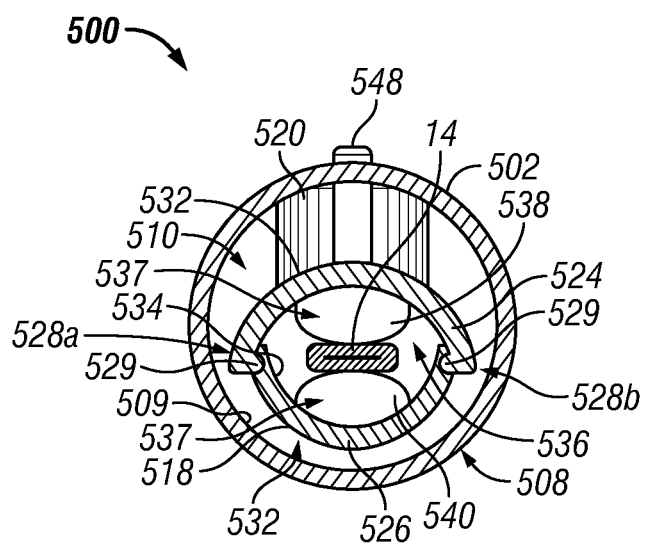
FIG. 9B is a cross-sectional view of a distal end of an embodiment of a clamp assembly shown in a sealing configuration in accordance with the present disclosure.

As best seen in FIG. 9A-B, the clamp assembly 500 includes a temporary clamping mechanism 537 that can be used to block flow of materials through the primary, secondary or tertiary tubes 12, 112, 212, 14, 114, 214, 40. More particularly, a first protrusion 538 is formed on the inner surface 534 of the top half portion 524 of the inner tube 518. The first protrusion 538 may be located at any location along the top half portion 524 of the inner tube 518, at or near the proximal end 528, at or near the distal end 530 or in a central region of the top half portion 524. In exemplary embodiments, the first protrusion 528 is located toward the distal end 530 of the top half portion 524, and could be at the distal end 530 or displaced from the distal end, so long as the first protrusion 538 is substantially beneath the first actuator 520 such that pressing the first actuator exerts a downward force on the first protrusion 538.

In exemplary embodiments, a second protrusion 540 is formed on the inner surface 534 of the bottom half portion 526 of the inner tube 518 toward the distal end of the bottom half portion 526. As with the first protrusion 538, the location of the second protrusion 540 on the bottom half portion 526 may vary. However, the second protrusion 540 should be substantially beneath the first protrusion 538 such that depressing the first actuator 520 and the first protrusion 538 causes the first protrusion to contact the second protrusion 540 so the two protrusions 538, 540 seal the inner lumen 536 of the inner tube 518. The first and second protrusions 538, 540 may be fixedly attached to or integrally formed with the top and bottom half portions 524, 526, respectively. The first actuator 520 may have an intermediate depressed position in which it is pressed down partially and the two protrusions 538, 540 form a temporary seal of the inner lumen 536. In a second, fully depressed position, the first actuator 520 is pressed down completely and the top and bottom half portions 524, 526 become locked.

Figure 10A:
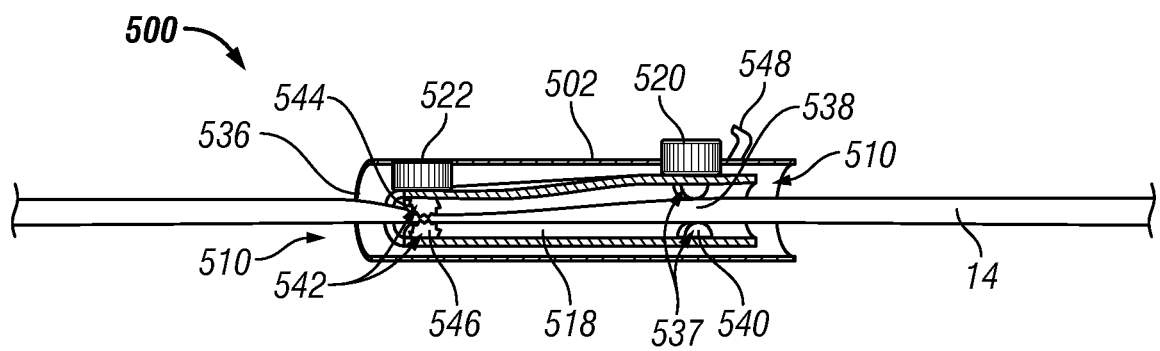
FIG. 10A is a side cutaway view of an embodiment of clamp assembly shown in a cutting configuration in accordance with the present disclosure.
Figure 10B:
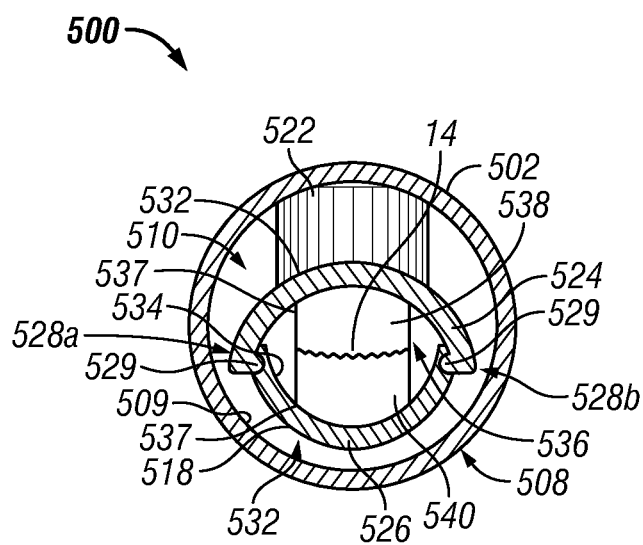
FIG. 10B is a cross-sectional view of a proximal end of an embodiment of a clamp assembly shown in a cutting configuration in accordance with the present disclosure.

In exemplary embodiments, the clamp assembly 500 comprises a cutting mechanism 542 at or near the proximal end 527 of the inner tube 518. As discussed in more detail herein, the cutting mechanism 542 allows the user to permanently sever a primary, secondary or tertiary tube 12, 112, 212, 14, 114, 214, 40 after use. As best seen in FIGS. 10A-B, exemplary embodiments of a cutting mechanism include a first cutting element 544 formed on the inner surface 534 of the top half portion 524 of the inner tube 518 and a second cutting element 546 formed on the inner surface 534 of the bottom half portion 526 of the inner tube. The cutting elements 544, 546 may be separate components fixedly attached to the inner tube 518 or integrally formed with the inner tube. The cutting elements may be blades made of metallic material or sharpened plastic materials and may be smooth or serrated.

The first cutting element 544 is located substantially beneath the second actuator 522 such that depressing the second actuator exerts a downward force on the first cutting element 544. The second cutting element 546 is located substantially beneath the first cutting element 544 so that depressing the second actuator 522 and the resulting downward cutting motion of the first cutting element 544 causes it to contact the second cutting element 546. If the clamp assembly 500 is mounted on a primary, secondary or tertiary tube, then the cutting elements 544, 546 would contact that tube, and this action would serve to cut a portion of primary, secondary or tertiary tube, as described in more detail herein. It should be noted that the cutting elements 544, 546 could be located at any portion of the inner tube 518 so long as they are substantially beneath one of the actuators 520, 522.

Exemplary embodiments of a clamp assembly 500 may further comprise a retaining clip 548 to hold the first actuator 520 down and lock it in a depressed position. The retaining clip 548 is located adjacent the first actuator 520 either proximal, distal or to the side of the first actuator 520. In exemplary embodiments, the retaining clip 548 is located just distal of the first actuator 520. As described in more detail herein, when the first actuator 520 is in a partially depressed position, the retaining clip 548 may be slid proximally to engage the first actuator 520 and hold its downward force on the first protrusion 538 to maintain the temporary seal of the inner lumen 536 of the inner tube 518 and thereby block flow of materials through one of the primary, secondary or tertiary tubes. The retaining clip 548 may be slid distally to disengage it from the first actuator 520 so the first actuator is raised and the inner lumen 536 is unsealed.

Figure 11A:
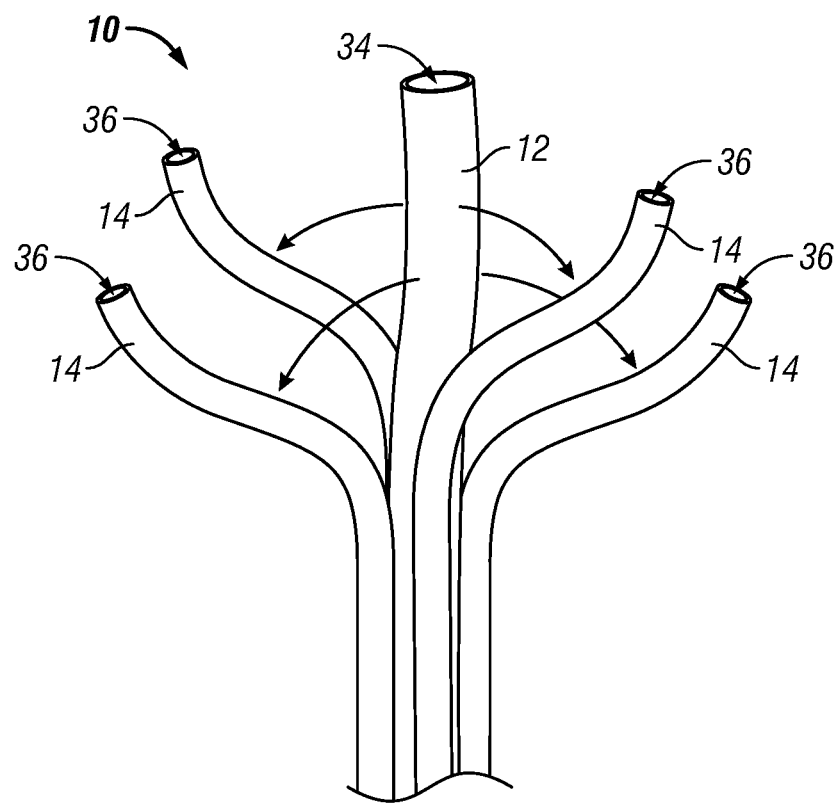
FIG. 11A is a perspective view of a proximal end of an embodiment of a mixing device in accordance with the present disclosure.
Figure 11B:
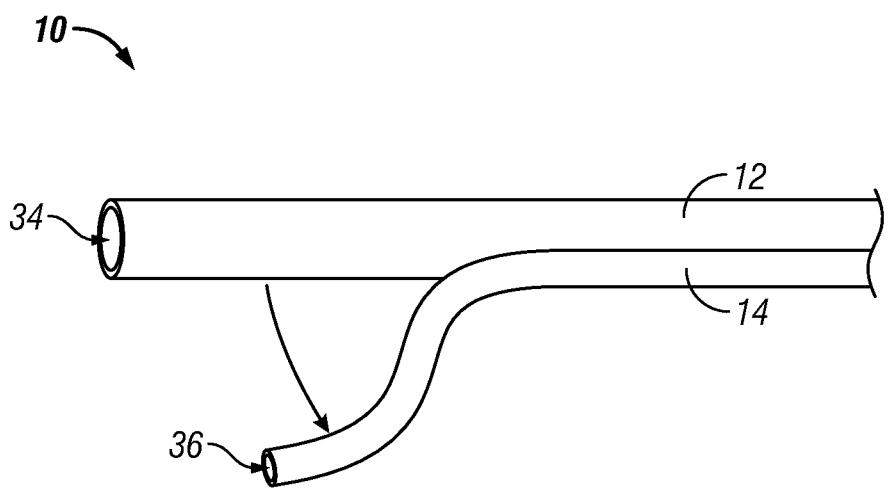
FIG. 11B is a perspective view of a proximal end of an embodiment of a mixing device in accordance with the present disclosure.
Figure 12:
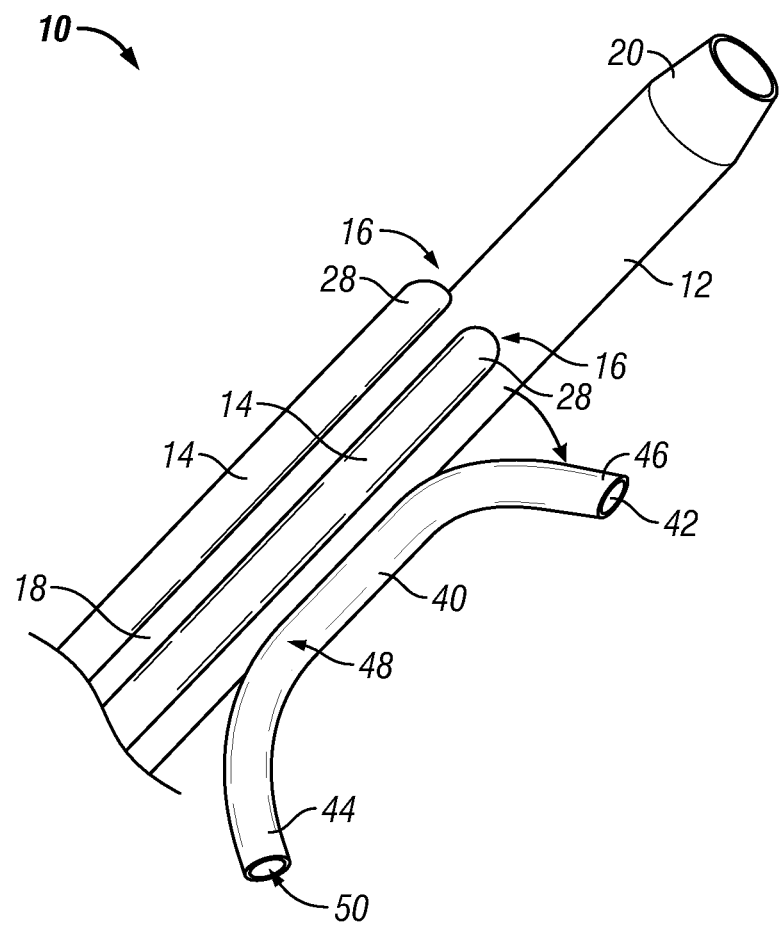
FIG. 12 is a perspective view of a distal end of an embodiment of a mixing device in accordance with the present disclosure.

Referring to FIGS. 11A-B, the secondary tubes 14 of mixing device 10 may be detachable so the user can peel them away after use. Turning to FIG. 12, it can be seen that an exemplary embodiment of a mixing device 10 may include at least one tertiary tube 40 that has a separate exit point 42 instead of a fluid connection with the primary tube 12. Like secondary tubes 14, tertiary tube 40 has a proximal end 44, a distal end 46, and outer surface 48 and defines an inner lumen 50. Tertiary tube 40 runs substantially parallel to the primary tube 12 and one or more secondary tubes 14. However, instead of its distal end 46 fluidly connecting to the primary tube 12 at a junction, tertiary tube 40 has its own separate and distinct exit point 42. This advantageously provides flexibility to the user so mixing device can be used in applications where certain fluids or materials need to be combined while other materials need to remain separate from the combined materials. In addition, the tertiary tube 40 could be detachable and peel away, as discussed in more detail with respect to intravenous fluid delivery system embodiments.

Figure 13A:
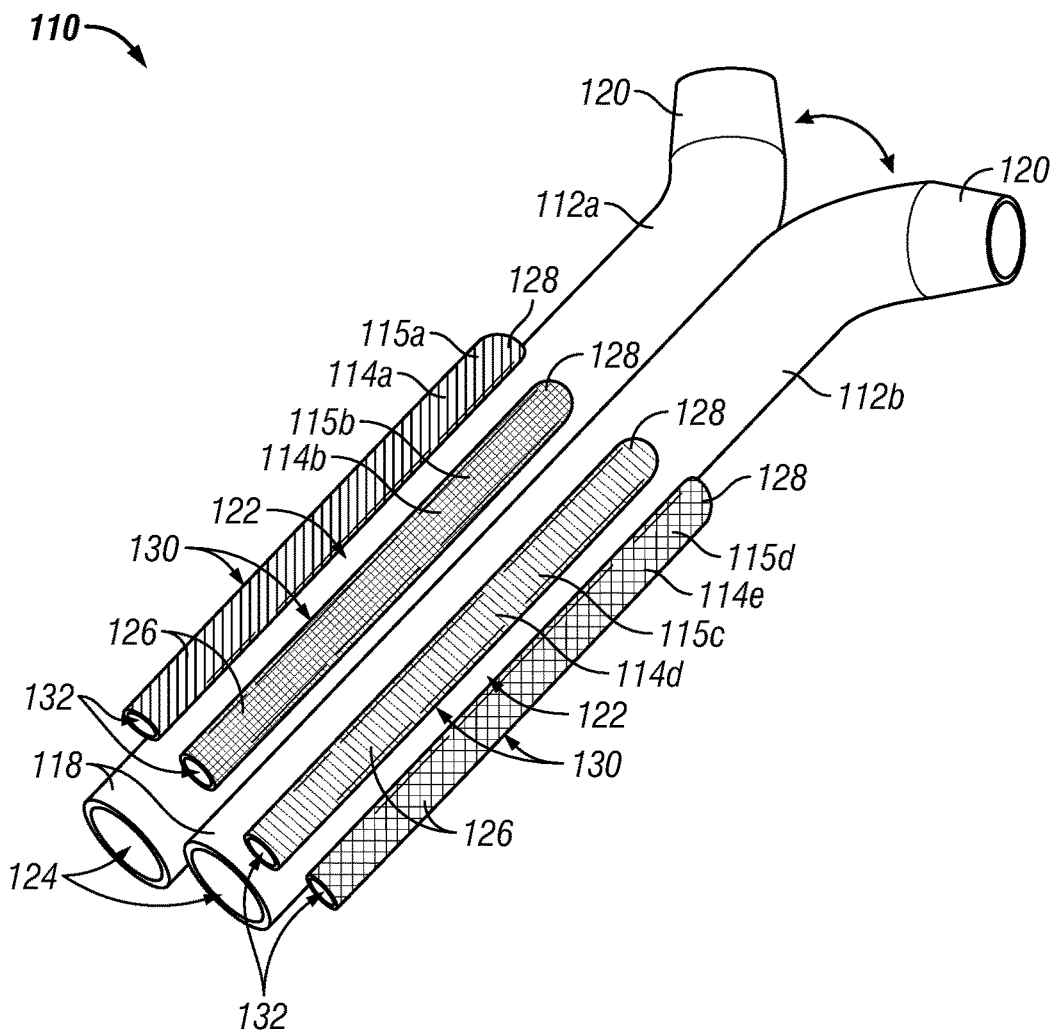
FIG. 13A is a perspective view of a distal end of an embodiment of a mixing device in accordance with the present disclosure.
Figure 13B:
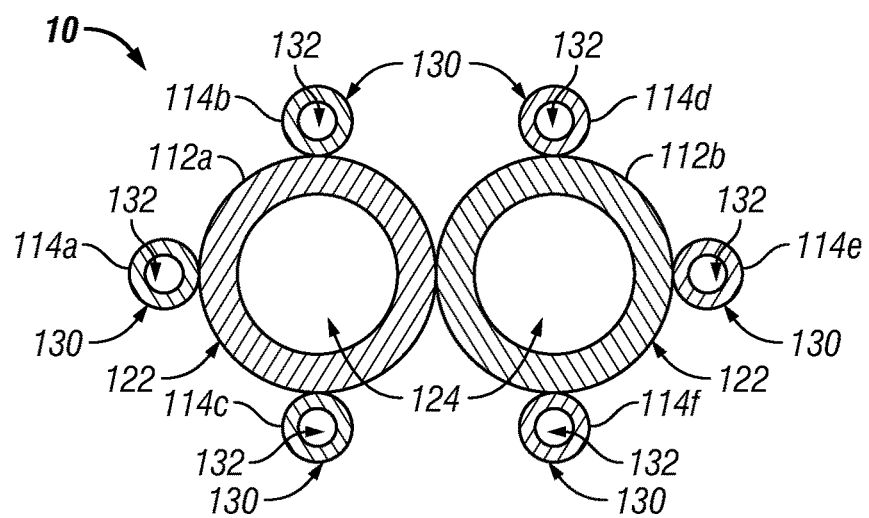
FIG. 13B is a cross-sectional view of the mixing device of FIG. 13A.
Figure 13C:
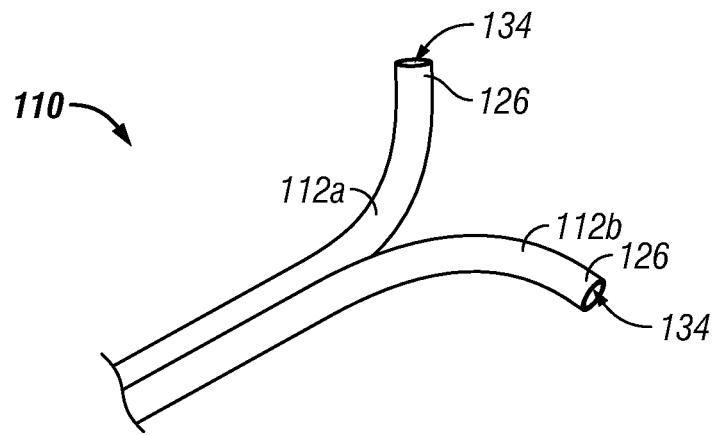
FIG. 13C is a perspective view of a proximal end of the mixing device of FIG. 13A.

As shown in FIGS. 13A-13C, exemplary embodiments of a mixing device 110 may have multiple primary tubes 112a, 112b running in parallel, with each primary tube 112a, 112b having one or more associated secondary tubes 114a-114c running substantially parallel to a respective primary tube 112a, 112b. Each primary tube 112a, 112b has a proximal end 118, a distal end 120, an outer surface 122 and defines an inner lumen 124. Each secondary tube is similarly configured with a proximal end 126, a distal end 128, an outer surface 130 and an inner lumen 132. In an exemplary embodiment, the outer surfaces 122a, 122b of the two primary tubes 112a, 112b are attached, either continuously or at multiple attachment points, and extend longitudinally in parallel configuration. As best seen in FIGS. 13A-13C, the primary tubes 112a, 112b could be configured to split apart at any point along their length, particularly at a point closer to the distal ends 128, and could also be releasably attached so they can be easily peeled away from each other. The primary tube 112 has one or more entry points 134, which could be any type of port for introducing fluid or materials, at or near its proximal end 126, and the secondary tube 114 has a distinct entry point 36 at its proximal end 126.

In exemplary embodiments, secondary tubes 114a, 114b, 114c may be attached to the outer surface 122 of the primary tube 112a, and secondary tubes 114d, 114e and 114f are attached to the outer surface of primary tube 112b. The secondary tubes 114a-f extend longitudinally along the outer surface 22 of the primary tube 112a, 112b and may be attached at one or more attachment points or have a continuous attachment along much of the length of the outer surface each respective primary tube 112 and secondary tube 114. One or more secondary tubes 114 may be removably attached to the primary tube 112 so they can be peeled away or detached from the primary tube 112 and discarded after the secondary tube has been used. Backflow prevention clamps or valves, sealing clamps or occlusion clamps could also be provided. Each primary tube 112a, 112b has a junction 116 close to its distal end 120 to provide a fluid connection between at least one secondary tube 114 and the primary tube 112a, 112b. The secondary tubes 114 could be color coded with the different colors 115a-115d (represented by different patterns in the figures) indicating different fluids or medications so the user can associate each secondary tube 114 with the particular chemical, medication or other material in that tube.

Figure 14:
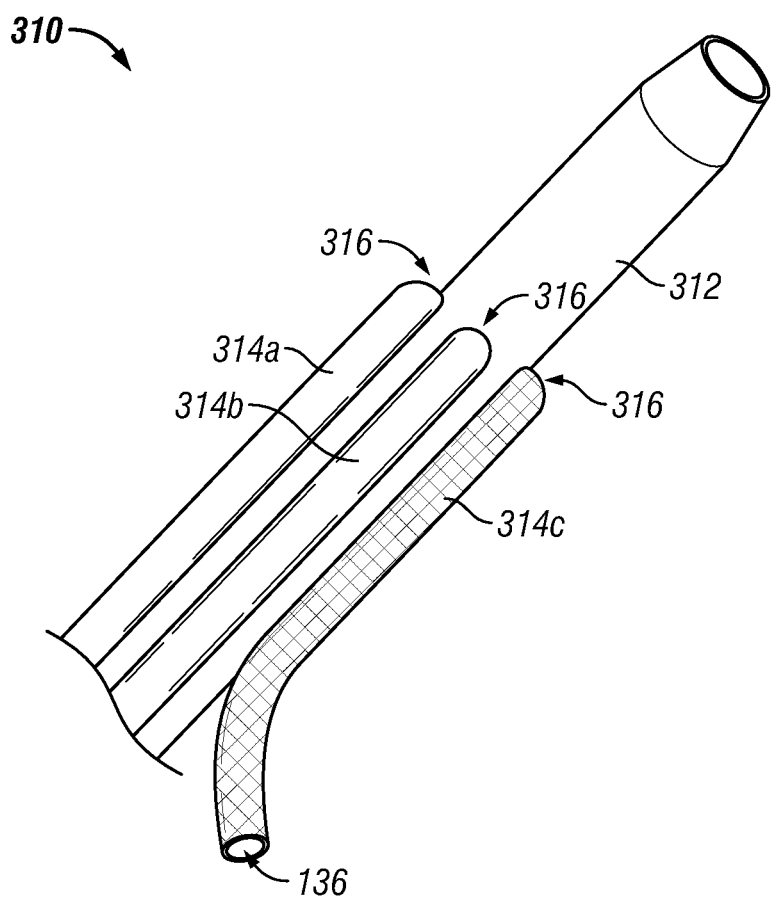
FIG. 14 is a perspective view of a distal end of an embodiment of a mixing device in accordance with the present disclosure.
Figure 15A:
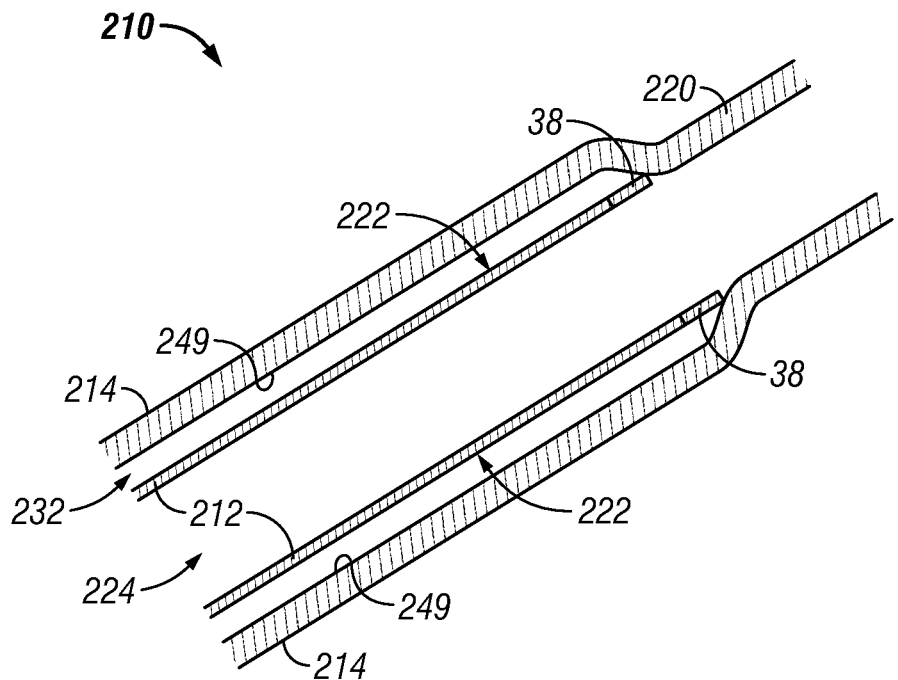
FIG. 15A is a side cross-sectional view of an embodiment of a mixing device in accordance with the present disclosure.
Figure 15B:
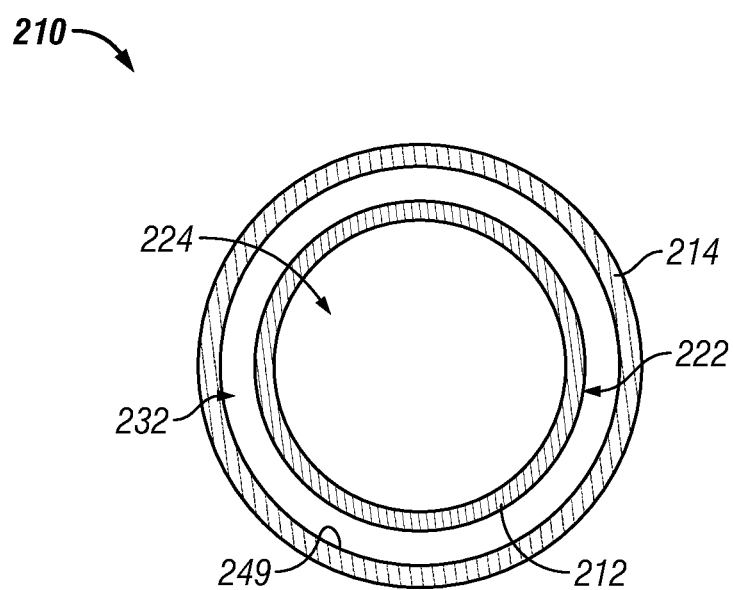
FIG. 15B is a rear cross-sectional view of the mixing device of FIG. 15A.
Figure 16A:
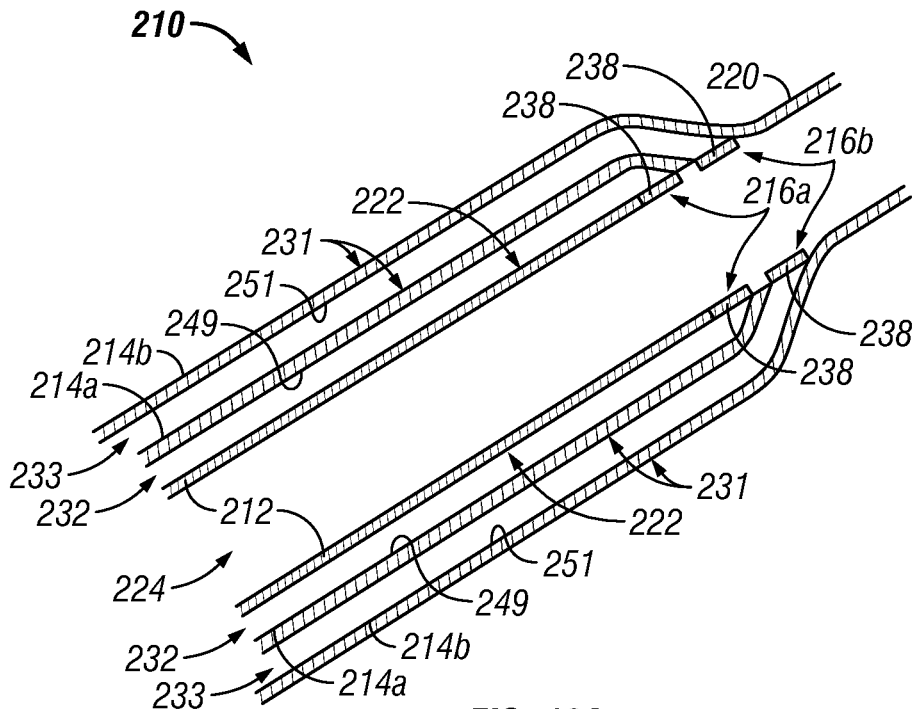
FIG. 16A is a side cross-sectional view of an embodiment of a mixing device in accordance with the present disclosure.
Figure 16B:
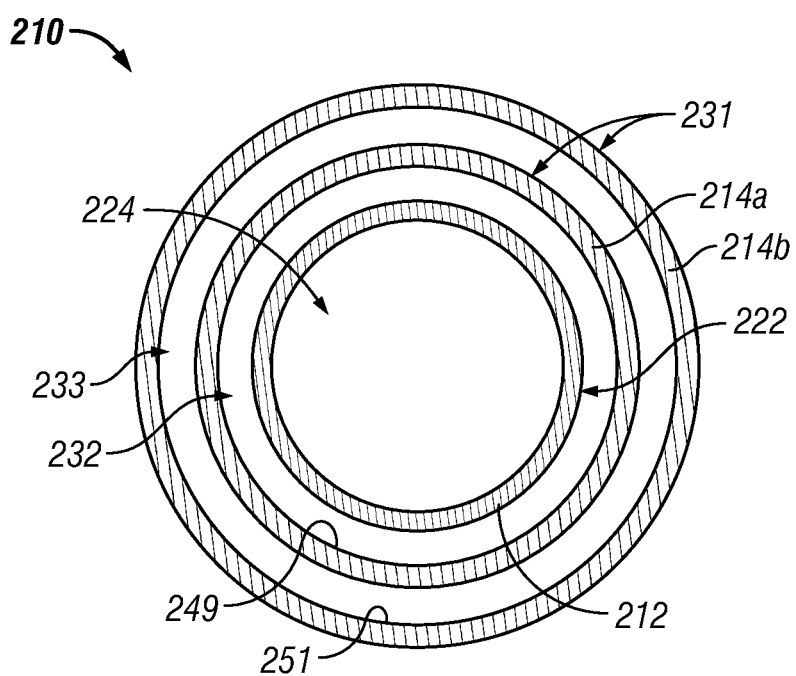
FIG. 16B is a rear cross-sectional view of the mixing device of FIG. 16A.
Figure 17A:
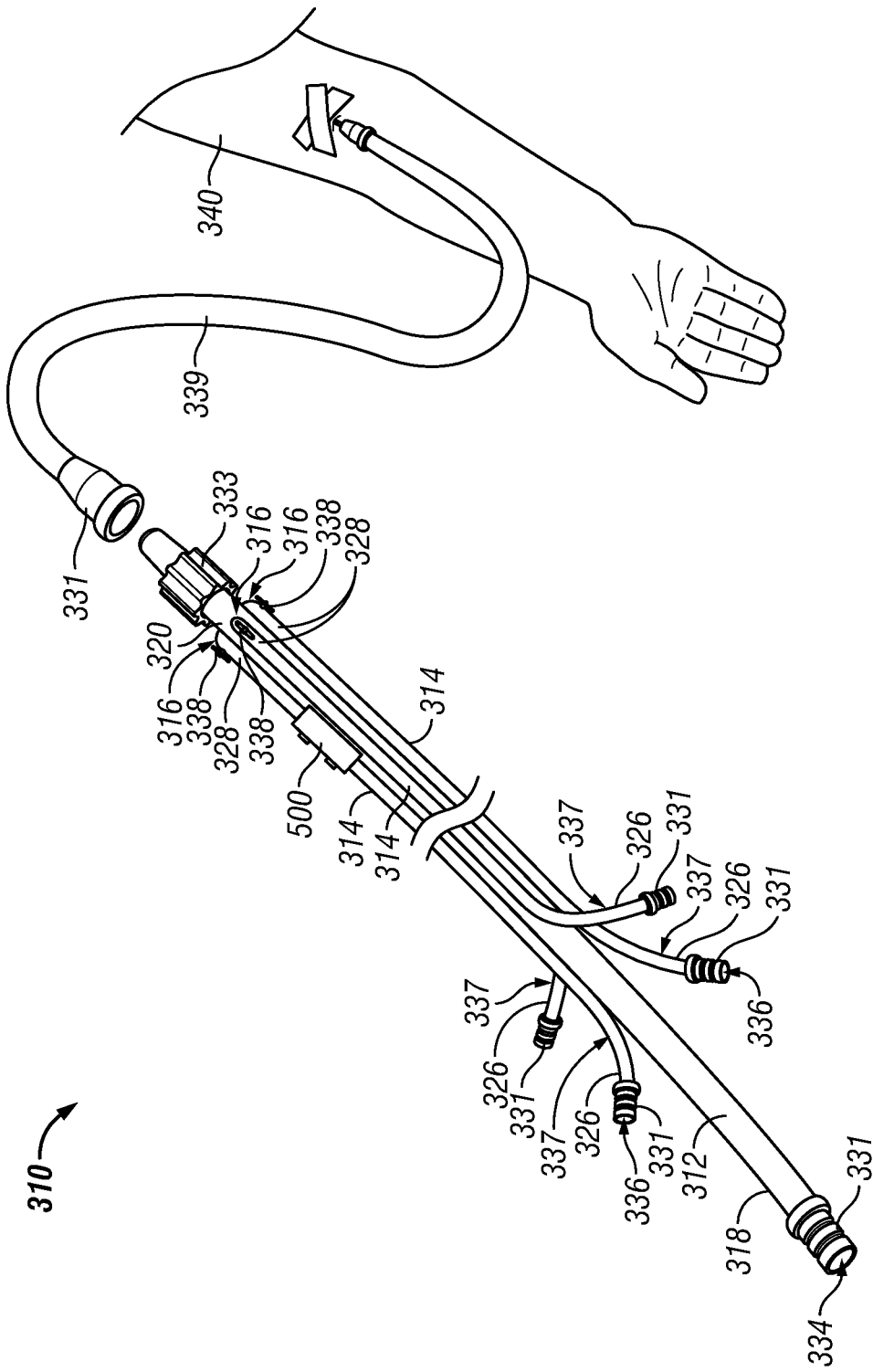
FIG. 17A is a perspective view of an embodiment of an intravenous fluid delivery system in accordance with the present disclosure.
Figure 17B:
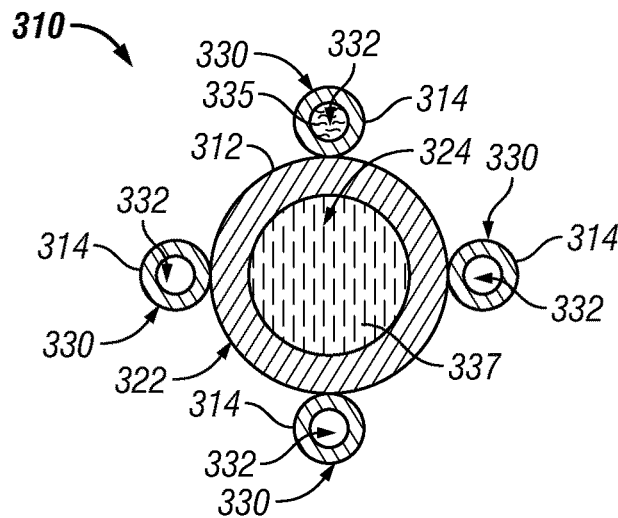
FIG. 17B is a cross-sectional view of the intravenous fluid delivery system of FIG. 17A.
Figure 18A:
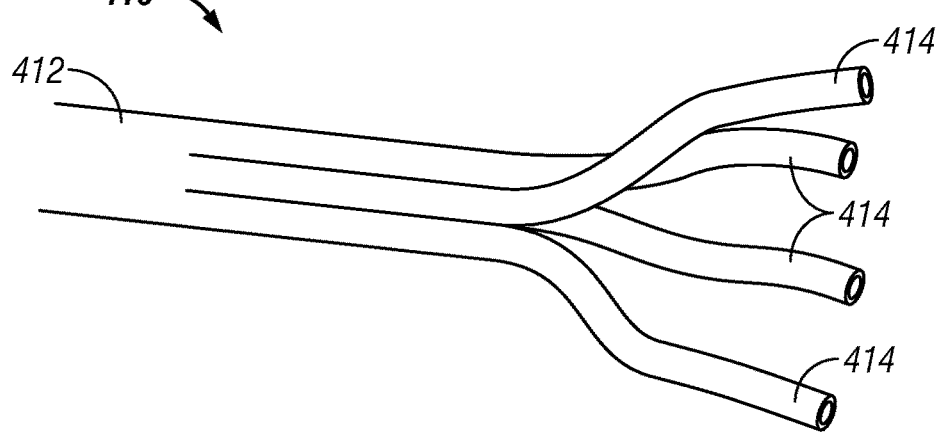
FIG. 18A is a perspective view of a proximal end of an embodiment of a mixing device in accordance with the present disclosure.
Figure 18B:
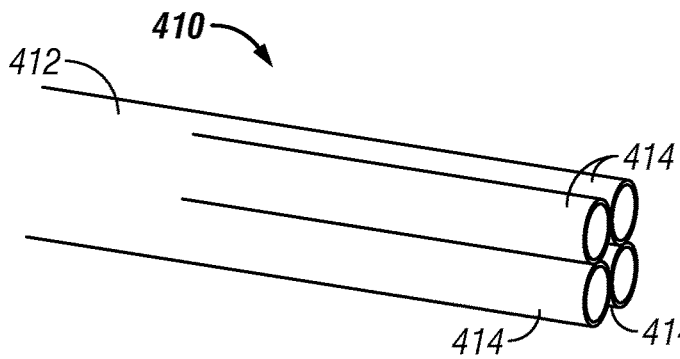
FIG. 18B is a perspective view of a distal end of the mixing device of FIG. 18A.
Figures 1, 18C:
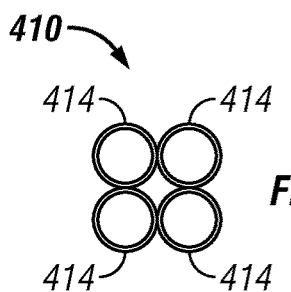
FIG. 18C-1 is a cross-sectional view of the proximal end of the mixing device of FIG. 18A.
Figures 2, 18C:
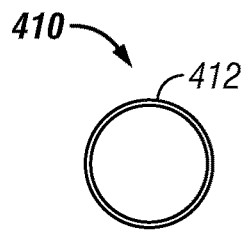
Figures 1, 19A:
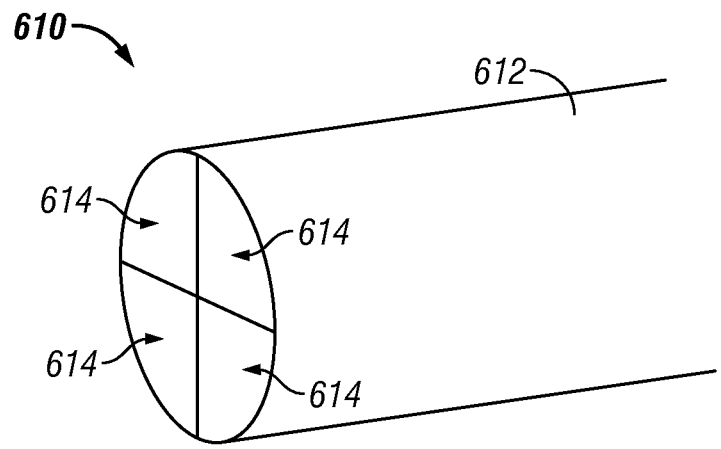
Figures 2, 19A:
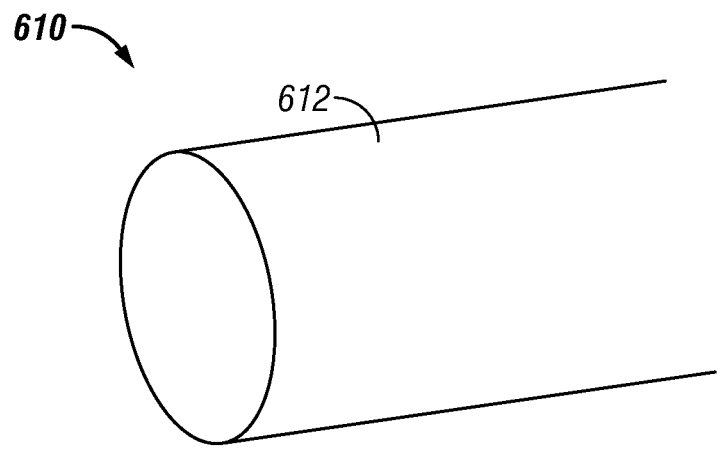
Figures 1, 19B:
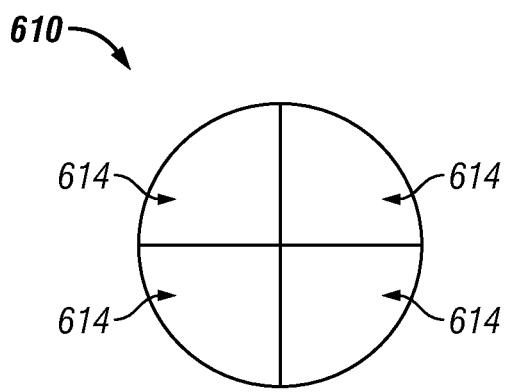
Figures 2, 19B:
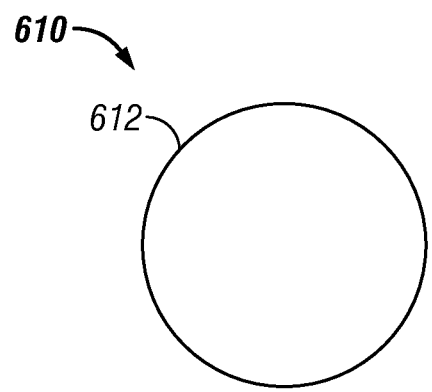
Figure 20A:
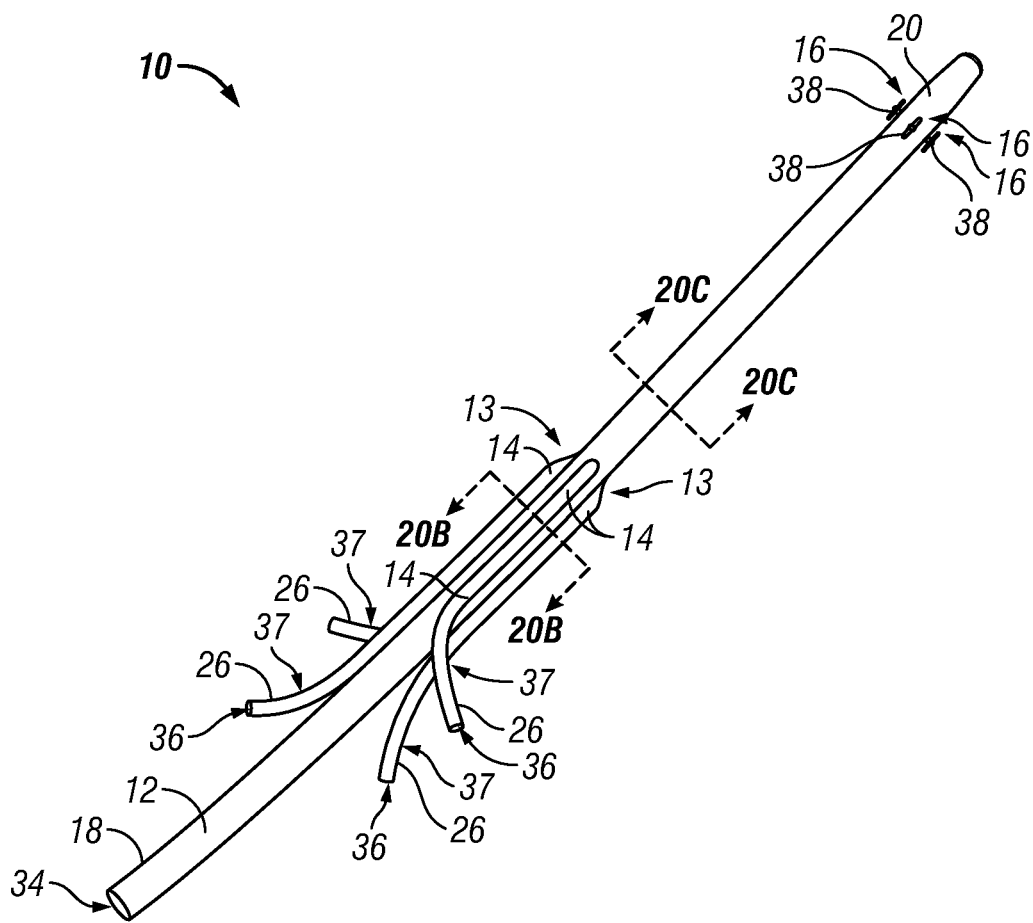
FIG. 20A is a perspective view of an embodiment of a mixing device in accordance with the present disclosure.
Figure 20B:
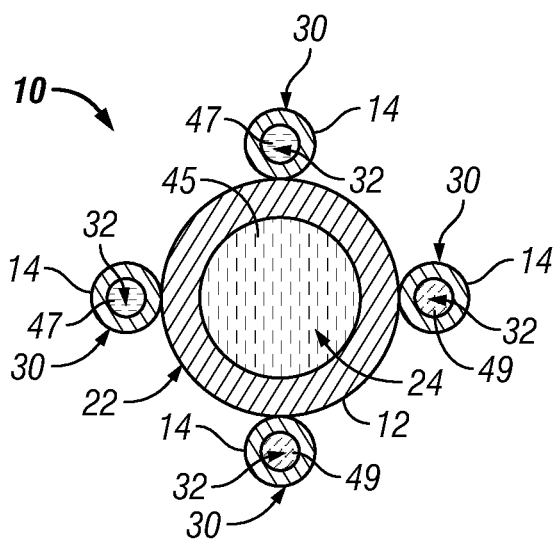
FIG. 20B is a cross-sectional view of the mixing device of FIG. 20A taken at section 20B-20B.
Figure 20C:
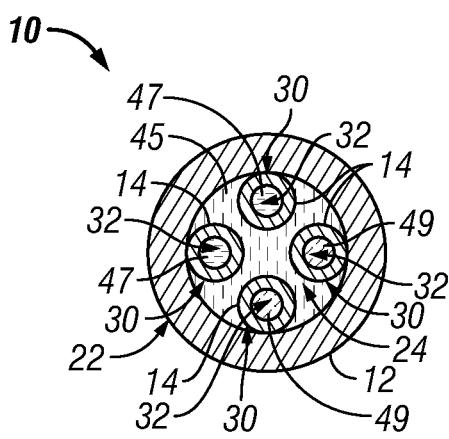
FIG. 20C is a cross-sectional view of the mixing device of FIG. 20A taken at section 20C-20C.
Figure 20D:
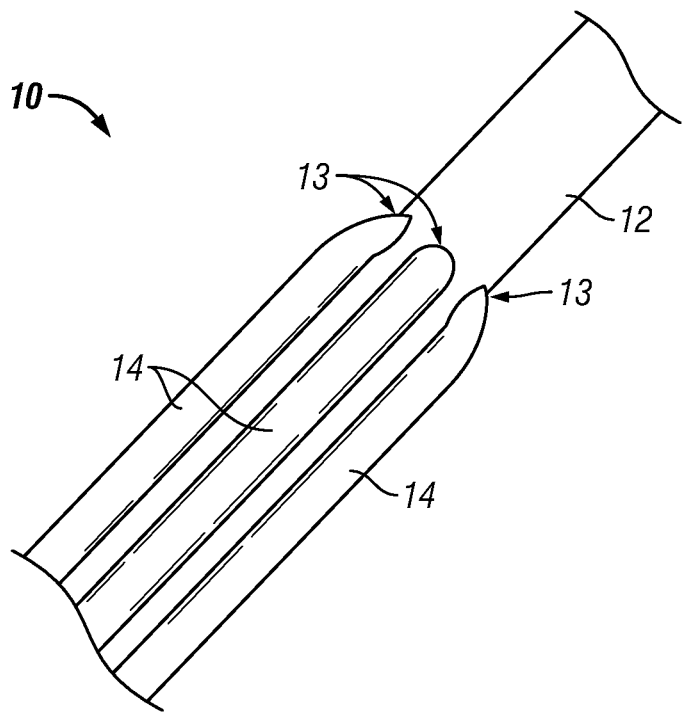
FIG. 20D is a perspective view of a junction point of the mixing device of FIG. 20A.
Figure 20E:
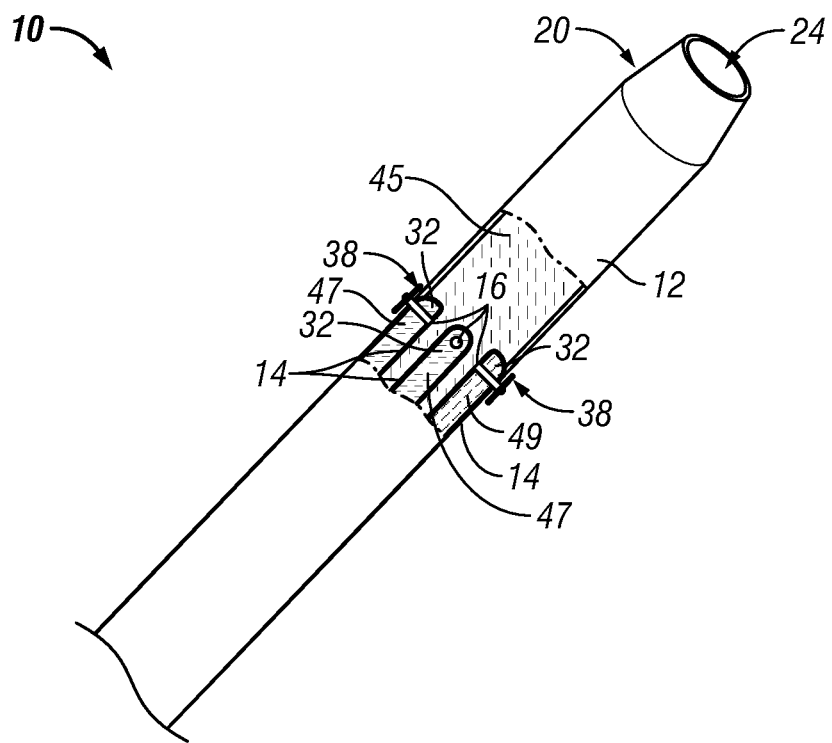
FIG. 20E is a cutaway view of a junction point of the mixing device of FIG. 20A.
Figure 21A:
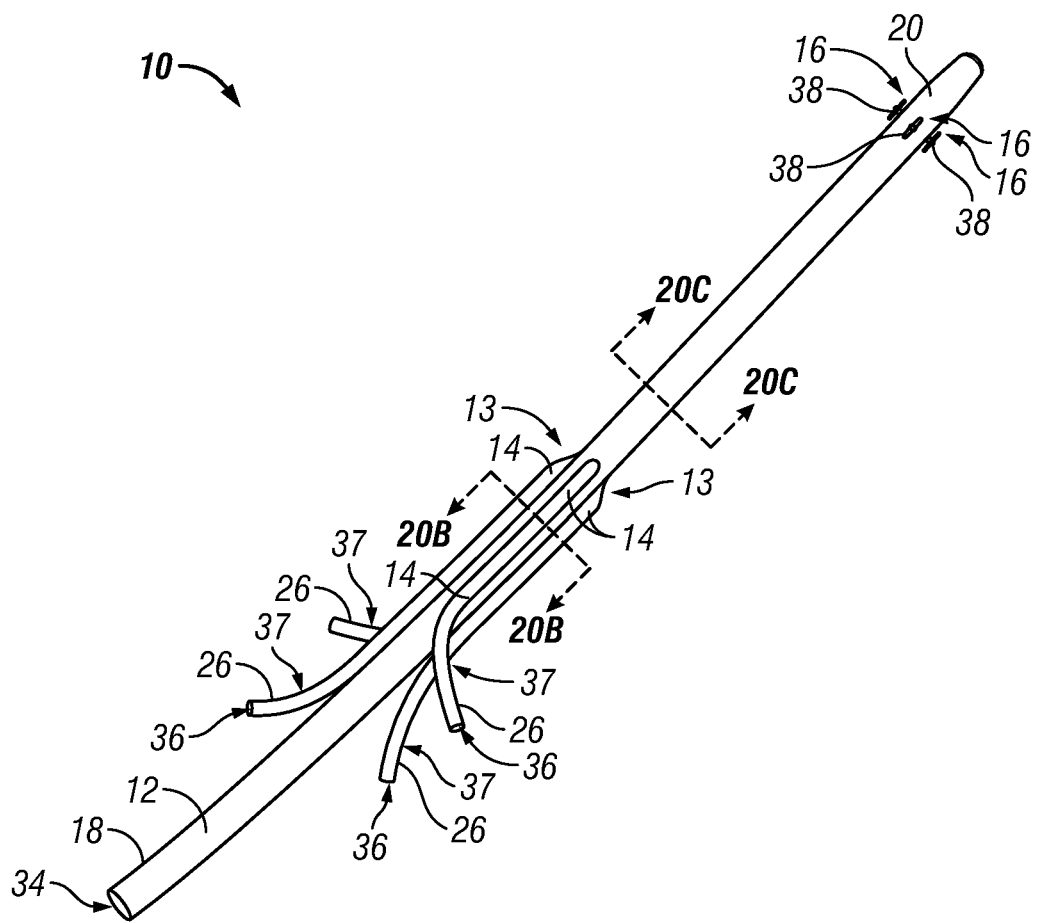
FIG. 21A is a perspective view of an embodiment of a mixing device in accordance with the present disclosure.
Figure 21B:
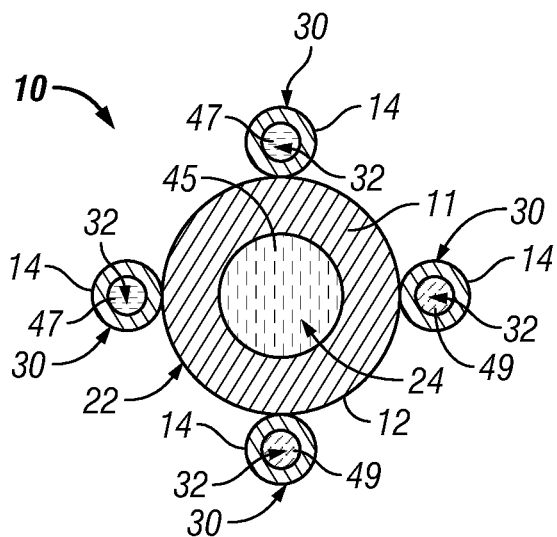
FIG. 21B is a cross-sectional view of the mixing device of FIG. 21A taken at section 21B-21B.
Figure 21C:
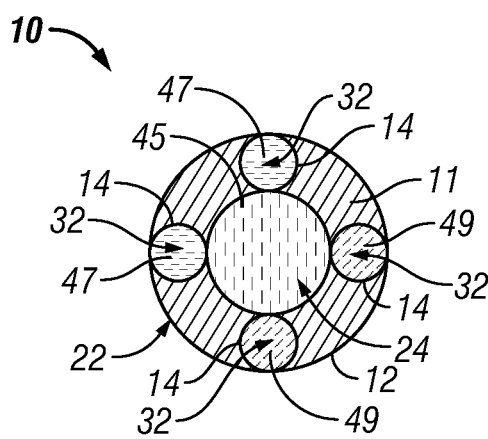
FIG. 21C is a cross-sectional view of the mixing device of FIG. 21A taken at section 21C-21C.
Figure 21D:
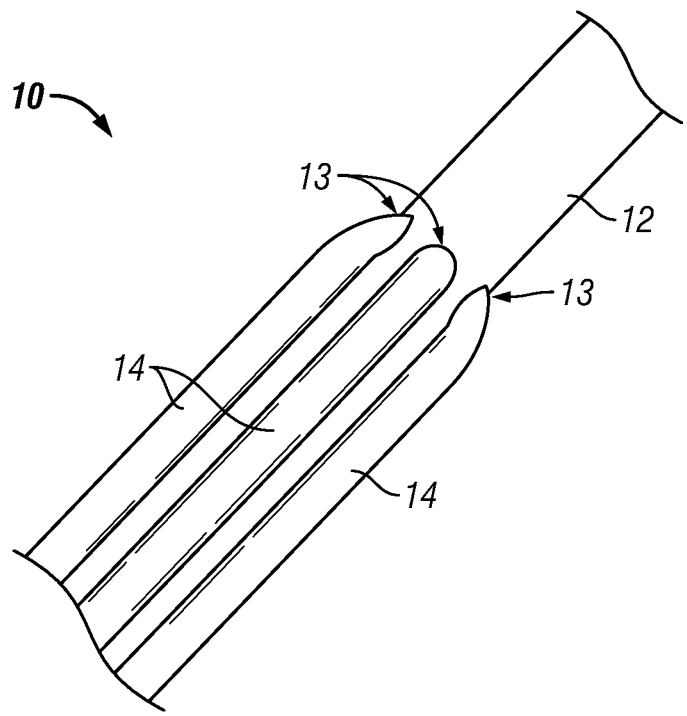
FIG. 21D is a perspective view of a junction point of the mixing device of FIG. 21A.
Figure 21E:
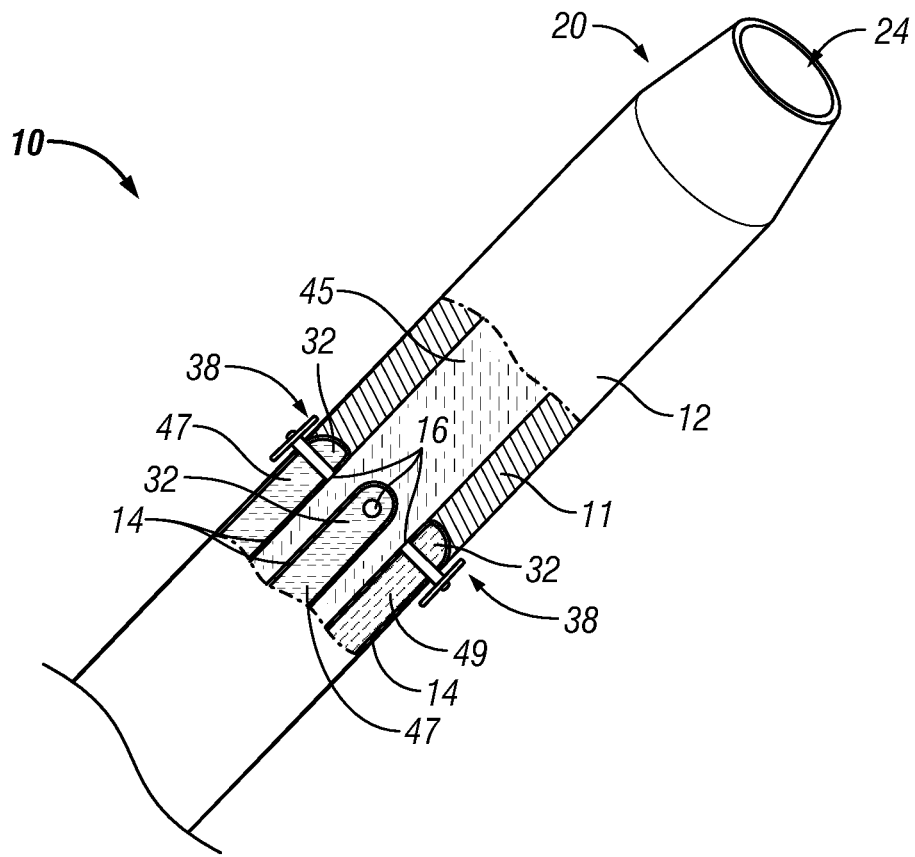
FIG. 21E is a cutaway view of a junction point of the mixing device of FIG. 21A.

Referring to FIG. 14, embodiments of a mixing device 310 may comprise one or more secondary tubes 314 made of a different material than the other secondary tube 314. For example, a secondary tube 314c may be made of low absorption material to minimize absorption of the fluid or medication running through the tube 314c. The secondary tube 314c may also be composed of low compliance tubing to allow for pressure transduction, i.e., arterial blood pressure monitoring, or measurement of other physiologic parameters such as arterial blood pressure monitoring.

In exemplary embodiments, the mixing device 210 may be configured in a co-axial arrangement. As shown in FIGS. 15A-16B, the primary tube 212 is an inner tube surrounded by one or more secondary tubes 214 such that the inner lumen 232 of the first secondary tube 214a is defined by the outer surface 222 of the primary tube 212 and the inner surface 249 of the first secondary tube 214a. The secondary tube 214a extends longitudinally along the outer surface 222 of the primary tube 212, and may be integrally formed with the primary tube 212. Exemplary embodiments may further comprise another secondary tube 214b surrounding the first secondary tube 214a such that the inner lumen 233 of the second secondary tube 214b is defined by the outer surface 231 of the first secondary tube 214a and the inner surface 251 of the secondary tube 214b. It should be understood that a co-axial mixing device 210 could include additional secondary tubes surrounding secondary tube 214b. One or more junctions 216a-b are located close to the distal end 220 of the primary tube 212 to provide a fluid connection between secondary tube 214a and the primary tube 212 and junction 216b provides a fluid connection between secondary tube 214b so a fluid or other material flowing through the secondary tubes 214a, 214b combines with a different fluid or material flowing through the primary tube 212 before the combined materials exit the distal end 220 of the primary tube 212. As discussed above, additional components to regulate and control the flow of materials from the secondary tubes 214 to the primary tube 212, such as back-flow clamps or valves, or occlusion clamps, may be provided.

In operation, the user introduces a first desired fluid, chemical or other material 45 into the mixing device 10 through entry point 34 of the primary tube 12. One or more secondary or tertiary materials 47, 49 are introduced into entry point 36 of the secondary tube 14. The secondary or tertiary materials 47, 49 could be introduced into the secondary tubes 14 at about the same time as the primary material 45 is introduced into the primary tube 12 or at different times. The timing depends on the particular purpose of the user, the nature of the application and the types of materials being used.

The first material 45 travels through the inner lumen 24 of the primary tube 12 from its proximal end 18 to its distal end 20. Concurrently or at a later time, the second material 46 travels through the inner lumen 32 of the secondary tube 14 from its proximal end 26 to its distal end 28. In exemplary embodiments, the user may maintains occlusion clamp 500 in a sealed position to prevent one or more of the secondary or tertiary materials 47, 49 in the secondary tubes 14 from mixing with the first material 45 in the primary tube. At the desired time for combining the secondary and/or tertiary materials 47, 49 with the primary material 44, the user opens the occlusion clamp 500 of one or more secondary tubes 14. This permits the secondary and/or tertiary materials 47, 47 to resume flow through junction 16 into the primary tube 12 and combine with the first material 45.

The user then may direct the combined materials through the distal end 20 of the primary tube 12 via a connector apparatus to other tubing, industrial, medical or scientific apparatus. When using embodiments of the invention having a tertiary tube 40, the user may direct a tertiary material 49 through the tertiary tube 40 and out the separate exit point 42. The user may also peel away and detach the tertiary tube 40 after completing the transfer of tertiary material 48 through it.

One or more clamp assemblies 500 may be used in conjunction with one or more of the tubes during operation to allow for temporary or permanent blocking of the flow of materials or to facilitate severance of one or more of the tubes. As discussed with reference to FIG. 7A-10C, an exemplary embodiment of a clamp assembly 500 may be threaded onto a secondary tube 14. If it is desired to temporarily seal the secondary tube 14, the user depresses the first actuator 520, which forces the first protrusion 538 downward and squeezes the secondary tube 14 between the first and second protrusion 538, 540, thereby sealing the secondary tube 14 and blocking the flow of material therein. The user may partially depress the first actuator 520 and hold it manually to temporarily block flow. Alternatively, the user may partially depress the first actuator 520 and slide the retaining clip 548 proximally so it engages the first actuator 520 and holds the first actuator 520 in the partially depressed position. To unseal the secondary tube 14 and restore the flow of materials therethrough, the user either releases the first actuator 520 directly or slides the retaining clip 548 distally to disengage it from the first actuator 520 and allow the first actuator 520 to rise from the partially depressed position.

If it is desired to permanently seal the secondary tube 14, the user presses the first actuator 520 to its fully depressed position. This action forces the first protrusion 538 downward and squeezes the secondary tube 14 between the first and second protrusion 538, 540, thereby sealing the secondary tube 14 to block the flow of material therein. This action also causes the top and bottom half portions 524, 526 to lock via the snap-fit engagement of male connecting portions 529 with female connecting portions 531 and stay in a compressed position.

If the user has finished using one or more of the primary, secondary or tertiary tubes in operation of the mixing device, a portion of a tube may be permanently severed using the clamp assembly 500. To cut secondary tube 14, the user depresses the second actuator 522, which causes a downward force on the first cutting element 544. The first cutting element 544 moves in a downward cutting motion toward the second cutting element 546 and the two cutting elements sever the secondary tube 14. The severed portion of the secondary tube 14 can then be discarded. The user may separate the outer sheath 502 from the inner tube 518 of the clamp 500 by sliding the outer sheath 502 in a proximal direction off the inner tube 518 and sliding the inner tube 518 in a distal direction. The sliding force causes linking mechanisms 503 to break, thereby decoupling the outer surface 532 of the inner tube 518 from the inner surface 509 of the outer sheath 502. The inner tube 518 of the occlusion clamp 500 remains coupled to the secondary tube 14 as cutting mechanism 542 of the occlusion clamp 500 will remain in a closed position to permanently seal the primary, secondary or tertiary tube at the severed end so the used tube can be discarded cleanly and safely without leakage of chemicals or other hazardous materials.

Referring now to FIGS. 1E, 2E, 3E, 4E and 17A-B, exemplary embodiments of a mixing device for use in intravenous (IV) fluid delivery applications will be described. An exemplary embodiment of an intravenous fluid delivery system 310 comprises at least one carrier line 312 and at least one administration line 314 fluidly connected to the primary tube at a junction 316. The carrier line 312 has a proximal end 318, a distal end 320, an outer surface 322 and defines an inner lumen 324. Similarly, the administration line 314 has a proximal end 326, a distal end 328, an outer surface 330 and defines an inner lumen 332. The carrier line 312 has an entry point 334, which could be any type of port suitable for introducing IV carrier fluids, nutrient fluids, medications or anesthetic agents, at its proximal end 326. In exemplary embodiments, there is a female Luer lock connector 331 to facilitate injection of fluids or medication into the carrier line. Each administration line 314 has a distinct entry point 336 at its proximal end 326 and may also include a Luer lock connector 331.

The administration line 314 runs substantially parallel to the carrier line 312, and in most medical uses fluids or medications traveling through the carrier and administration lines 312, 314 flow in the same direction. The secondary tube 314 may be attached to the outer surface 322 of the primary tube 312. In exemplary embodiments, the administration line 314 extends longitudinally along the outer surface 318 of the carrier line 312, and may be attached at one or more attachment points or have a continuous attachment along much of the length of the outer surface of the carrier line 312 and administration 314. One or more of the administration lines 314 may have a bend or kink 337 to facilitate access of materials into entry point 336. In addition, one or more of the administration lines 314 may be removably attached to the carrier line 312 so they can be peeled away or detached from the carrier line 312 and discarded after one or more of the administration lines 314 have been used.

In exemplary embodiments, IV fluid delivery system has a junction 316 at or near the distal end 320 of the carrier line 312. The junction 316 provides a fluid connection between at least one administration line 314 and the carrier line 312 so a second IV fluid or medication that flows through the administration line 314 mixes with a first IV fluid or medication that flows through the carrier line 312. Each junction 316 is spaced slightly proximal of the distal end 320 of the carrier line 312 so the fluids or medications from one or more administration lines 314 can enter the carrier line 312 and combine with the carrier fluid in the carrier line 312 immediately before the combined materials exit the distal end 320 of the carrier line 312. The distal end of the carrier line 312 may be fitted with a male Luer lock connector 333 to facilitate a connection to an IV tube 339 entering the patient 340.

As discussed with reference to FIGS. 5-6, mechanisms to prevent back-flow of the carrier fluid or other material from the carrier line into the administration lines may be provided. The IV delivery system 310 could also include an occlusion clamp 500. In exemplary embodiments, the occlusion clamp 500 is coupled to the secondary tube 314 to seal the tube and stop the flow of IV fluids or medications from passing through junction 316 to the carrier line 312. Embodiments of an occlusion clamp 500 are described in detail above in connection with FIGS. 7A-10C, so will not be comprehensively described again here.

It should be noted that each and every embodiment and variation of a mixing device described above could be used in conjunction with an IV delivery system and some embodiments may be particularly advantageous in IV applications. For instance, as discussed with reference to FIG. 12, one or more of the administration lines could have a separate and distinct exit point instead of a fluid connection with the carrier line and could be detachable so the medical practitioner could peel it away and discard the administration line after use. This advantageously provides flexibility to the medical practitioner in applications where certain IV fluids or medications need to be combined while other IV materials need to remain separate from the combined fluids or medications.

In addition, an IV delivery system may comprise multiple carrier lines running in parallel, each having one or more associated administration lines running substantially parallel to a respective carrier line. As best seen in FIGS. 13A-13C, the carrier lines could be configured to split apart at any point along their length, particularly at a point closer to the distal ends, and could also be releasably attached so the medical practitioner can easily peel the carrier lines away from each other. The administration lines could be color coded with the different colors (represented by different patterns in the figures) indicating different IV fluids or medications. As shown in FIG. 14, one of the administration lines could be made of a different material than the other administration lines such as a low absorption material for more effective delivery of medications that are absorbed by standard tubing material or low-compliance tubing to allow for pressure transduction or measurement of other physiologic parameters such as arterial blood pressure monitoring. Referring again to FIGS. 15A-16B, an IV delivery system could also have a co-axial configuration such that the carrier line is an inner tube surrounded by one or more administration lines.

In operation, the medical practitioner introduces carrier fluid 339 into the carrier line 312 through female Luer lock connector 331 so the carrier fluid 337 flows through the inner lumen 324 of the carrier line 312 and into the patient 340. At any time before it is necessary to administer additional IV fluids or IV medication 335, the medical practitioner introduces one or more of such fluids or medications into a respective administration line 314. Backflow prevention mechanisms 338 may be used to ensure that the carrier fluid 337 does not flow backwards into any of the administration lines 314.

The medical practitioner may employ an occlusion clamp 500 by threading it onto one or more of the administration lines 314 to a desired location on the administration line 314 so the administration line runs through the inner lumen 536 of inner tube 518. To prevent the flow of IV fluid or medication 335 from the administration line 314 into the carrier line 312, the medical practitioner uses the temporary clamping mechanism 537 by pressing the first actuator 520 down into an intermediate position. This causes the first protrusion 538 to move downward and squeeze a portion of the administration line 314 between the first and second protrusions 538, 540, thereby temporarily sealing the administration line 314. The medical practitioner may slide the retaining clip 548 in a proximal direction to hold down the first actuator 520 and maintain the seal.

When the medical practitioner is ready to administer the IV fluid or medication 335 in the administration line 314, he or she either manually releases the first actuator 520 or slides the retaining clip 548 in a distal direction to disengage it from the first actuator. This causes the first protrusion 538 to rise and unseals the administration line 314 to restore flow of the IV fluid or medication 335. The IV fluid or medication 335 then flows distally through the inner lumen 332 of the administration line 314 and through junction 316 into the carrier line 312. There the IV fluid or medication 335 mixes with the carrier fluid 337 flowing through the inner lumen 324 of the carrier line 312. The combined carrier fluid 337 and IV fluid or medication 335 then exit the distal end 320 of the carrier line 312 through male Luer lock connector 333 and flows into the patient 340.

If using a peel away embodiment, the medical practitioner may then simply peel away the used administration line 314 after the IV fluid or medication 335 has been administered. Alternatively, the medical practitioner could sever the used administration line 314 using the cutting mechanism cutting mechanism 542 of the occlusion clamp 500. This can be accomplished by depressing the second actuator 522, which causes cutting element 544 to move downward toward cutting element 546, thereby cutting through the portion of the administration line 314. The medical practitioner can sever at any point along the administration line 314 by sliding the occlusion clamp 500 along the line to the desired point and then depressing the second actuator 522 when the desired point is reached. This advantageously allows the medical practitioner the flexibility cut or peel away all of the used administration line 314 or just a portion of it. The cutting mechanism 542 of the occlusion clamp 500 will remain in a closed position to permanently seal the administration line 314 at the severed end so the used administration line 314 can be discarded cleanly and safely without leakage of fluids or medication.

It will be apparent to those skilled in the art that the selective separation and attachment points of the carrier line and the administration lines makes the IV delivery system particularly advantageous for medical uses. The system is both efficient and easy to use due to its a compact, integrated design with the tubes attached in a single unit, and with selective flow control and administration line peel away capability. The system provides an IV fluid and medication delivery system that is safe during use and safe to clean up.

Thus, it is seen that mixing systems and methods for research, industrial and medical uses are provided. It should be understood that any of the foregoing configurations and specialized components or chemical compounds may be interchangeably used with any of the systems of the preceding embodiments. Although illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention.

What is claimed is:

1. An intravenous fluid or medication delivery apparatus comprising:
   a central primary tube carrying a first intravenous fluid or medication and having a proximal end, a distal end, an outer surface and defining an inner lumen;
   at least one secondary tube carrying a second intravenous fluid or medication different than the first intravenous fluid or medication and having a proximal end, a distal end, a length between and defined by the proximal and distal ends of the at least one secondary tube, an outer surface and defining an inner lumen, the at least one secondary tube being directly and fixedly attached to the primary tube such that a majority portion of the length of the at least one secondary tube is in direct contact with the primary tube and the at least one secondary tube runs substantially parallel to the primary tube, the distal end of the at least one secondary tube being fluidly connected to the primary tube at a junction such that the second intravenous fluid or medication in the at least one secondary tube flows into the primary tube and mixes with the first intravenous fluid or medication, the junction being located close to the distal end of the primary tube; and
   at least one tertiary tube having a proximal end, a distal end, an outer surface and defining an inner lumen, the at least one tertiary tube not being fluidly connected to the primary tube and having a separate and distinct exit point from an exit point of the primary tube.

2. The apparatus of claim 1 wherein the primary tube and the at least one secondary tube have separate and distinct entry points at their proximal ends.

3. The apparatus of claim 1 further comprising a backflow prevention mechanism coupled to the apparatus.

4. The apparatus of claim 1 further comprising a connector apparatus attached to the distal end of the primary tube.

5. The apparatus of claim 1 wherein the at least one secondary tube comprises a plurality of secondary tubes.

6. The apparatus of claim 5 wherein at least one of the plurality of secondary tubes is attached to the outer surface of the primary tube and extends longitudinally along the outer surface of the primary tube.

7. The apparatus of claim 6 wherein at least one of the plurality of secondary tubes peels away from the primary tube at or near the proximal end of at least one of the plurality of secondary tubes.

8. The apparatus of claim 1 wherein the at least one tertiary tube is substantially parallel to the primary tube and the at least one secondary tube.

9. The apparatus of claim 1 wherein one or more of the primary tube and the at least one secondary tube is color-coded.

10. The apparatus of claim 1 further comprising a sealing clamp coupled to one or more of the primary tube and the at least one secondary tube.

11. An intravenous fluid delivery system, comprising:
    at least one carrier line carrying a first intravenous fluid or medication and having a proximal end, a distal end, an outer surface and defining an inner lumen;
    at least one first administration line carrying a second intravenous fluid or medication different than the first intravenous fluid or medication and having a proximal end, a distal end, a length between and defined by the proximal and distal ends of the at least one first administration line, an outer surface and defining an inner lumen, the at least one first administration line being directly and fixedly attached to the at least one carrier line such that a majority portion of the length of the at least one first administration line is in direct contact with the at least one carrier line and the at least one first administration line runs substantially parallel to the at least one carrier line along substantially the entire length of the at least one first administration line, the distal end of the at least one first administration line being fluidly connected to the at least one carrier line at a junction such that the second intravenous fluid or medication in the at least one first administration line flows into the at least one carrier line and mixes with the first intravenous fluid or medication, the junction being located close to the distal end of the at least one carrier line; and
    at least one second administration line having a proximal end, a distal end, an outer surface and defining an inner lumen, the at least one second administration not being fluidly connected to the at least one carrier line and having a separate and distinct exit point from an exit point of the at least one carrier line.

12. The system of claim 11 wherein the at least one carrier line and the at least one first administration line have separate and distinct fluid entry ports at their proximal ends.

13. The system of claim 11 wherein the at least one first administration line comprises a plurality of administration lines.

14. The system of claim 13 wherein at least one of the plurality of administration lines is attached to the outer surface of the at least one carrier line and extends longitudinally along the outer surface of the at least one carrier line.

15. The system of claim 11 further comprising a connector apparatus attached to the distal end of the at least one carrier line, the connector apparatus being configured to connect the at least one carrier line to an intravenous fluid transfer component.

16. The system of claim 11 wherein the at least one secondary administration line is substantially parallel to the at least one carrier line.

17. The system of claim 11 wherein the at least one carrier line comprises two or more bundled carrier lines and the at least one first administration line comprises two or more first administration lines, each carrier line having at least one of the first administration lines fluidly connected thereto.

18. The system of claim 11 further comprising an occlusion clamp assembly coupled to one or more of the at least one carrier line and the at least one first administration line.

19. The system of claim 11 wherein one or more of the at least one carrier line and the at least one first administration line is made of a low absorption material.

\* \* \* \* \*